(12) United States Patent
Rush et al.

(10) Patent No.: US 10,334,230 B1
(45) Date of Patent: Jun. 25, 2019

(54) IMAGE CAPTURE SYSTEM

(71) Applicant: Nebraska Global Investment Company, LLC, Lincoln, NE (US)

(72) Inventors: Benjamin D. Rush, Lincoln, NE (US); Joshua M. Brown-Kramer, Lincoln, NE (US); Lucas A. Sabalka, Lincoln, NE (US); Nathan H. Lowry, Lincoln, NE (US)

(73) Assignee: Nebraska Global Investment Company, LLC, Lincoln, NE (US)

( * ) Notice: Subject to any disclaimer, the term of this patent is extended or adjusted under 35 U.S.C. 154(b) by 0 days.

(21) Appl. No.: 14/713,659

(22) Filed: May 15, 2015

Related U.S. Application Data

(63) Continuation of application No. 13/690,261, filed on Nov. 30, 2012, now Pat. No. 9,072,929.

(60) Provisional application No. 61/709,354, filed on Oct. 4, 2012, provisional application No. 61/670,317, filed on Jul. 11, 2012, provisional application No. 61/583,241, filed on Jan. 5, 2012, provisional application No. 61/565,865, filed on Dec. 1, 2011.

(51) Int. Cl.
*G06K 9/00* (2006.01)
*H04N 13/25* (2018.01)
*H04N 13/257* (2018.01)
*H04N 13/282* (2018.01)

(52) U.S. Cl.
CPC ........... *H04N 13/25* (2018.05); *H04N 13/257* (2018.05); *H04N 13/282* (2018.05); *H04N 2213/003* (2013.01)

(58) Field of Classification Search
None
See application file for complete search history.

(56) References Cited

U.S. PATENT DOCUMENTS

| | | | | |
|---|---|---|---|---|
| 5,579,444 A | * | 11/1996 | Dalziel | B25J 9/1669 382/153 |
| 6,950,534 B2 | * | 9/2005 | Cohen | G06F 3/017 382/103 |
| 7,277,558 B2 | * | 10/2007 | Sefcik | G06T 7/20 348/169 |

(Continued)

OTHER PUBLICATIONS

Liu et al ("Hand Gesture Recognition using Depth Data", 2004).*

(Continued)

*Primary Examiner* — Avinash Yentrapati

(57) ABSTRACT

A system is described that allows for the tracking of an exercise occurring within a physical environment. In one or more implementations, the system includes a depth sensing device configured to obtain depth values associated with a plurality of pixels. The depth values indicating distances from one or more physical objects in a physical environment to the depth sensing device. The system also includes a computing device in communication with the depth sensing device. The computing device includes a memory and a processor. The processor is configured to execute the one or more modules to cause the processor to: identify a point corresponding to at least one pixel representing a portion of at least one physical object within the physical environment based upon the pixel depth values; track the point through a plurality of image frames; and determine whether at least one repetition has occurred based upon the tracked point.

19 Claims, 11 Drawing Sheets

(56) References Cited

U.S. PATENT DOCUMENTS

| | | | | |
|---|---|---|---|---|
| 7,372,977 B2* | 5/2008 | Fujimura | ........... | G06K 9/00369 |
| | | | | 382/103 |
| 7,650,017 B2* | 1/2010 | Yamada | ............ | G06K 9/00248 |
| | | | | 345/156 |
| 7,840,031 B2* | 11/2010 | Albertson | .......... | A63B 24/0003 |
| | | | | 382/103 |
| 8,184,857 B2* | 5/2012 | Akita | ...................... | G06T 7/269 |
| | | | | 348/143 |
| 8,238,639 B2* | 8/2012 | Silver | .................. | G06K 9/6202 |
| | | | | 382/141 |
| 8,520,895 B2* | 8/2013 | Au | ............................. | G01P 3/38 |
| | | | | 235/400 |
| 8,744,121 B2* | 6/2014 | Polzin | ................ | G06K 9/00342 |
| | | | | 382/103 |
| 8,745,541 B2* | 6/2014 | Wilson | .................... | G06F 3/017 |
| | | | | 345/156 |
| 8,891,825 B2* | 11/2014 | Baele | ................ | G06K 9/00201 |
| | | | | 382/103 |
| 8,963,829 B2* | 2/2015 | Lee | ......................... | G06F 3/017 |
| | | | | 345/156 |
| 8,970,487 B2* | 3/2015 | Leyvand | ................ | G06K 9/469 |
| | | | | 345/156 |
| 9,129,506 B1 | 9/2015 | Kusens | | |
| 9,159,215 B1 | 10/2015 | Kusens | | |
| 9,165,449 B2 | 10/2015 | Ribble et al. | | |
| 9,204,823 B2 | 12/2015 | Derenne et al. | | |
| 2004/0247157 A1* | 12/2004 | Lages | ..................... | G01S 17/89 |
| | | | | 382/103 |
| 2005/0058322 A1* | 3/2005 | Farmer | ................ | G06K 9/3233 |
| | | | | 382/103 |
| 2005/0238201 A1* | 10/2005 | Shamaie | ............ | G06K 9/00335 |
| | | | | 382/103 |
| 2006/0056689 A1* | 3/2006 | Wittebrood | ........... | G06T 7/0081 |
| | | | | 382/173 |
| 2006/0239558 A1* | 10/2006 | Rafii | .................. | G06K 9/00201 |
| | | | | 382/181 |
| 2008/0170748 A1* | 7/2008 | Albertson | ................ | G06F 3/017 |
| | | | | 382/103 |
| 2009/0147994 A1* | 6/2009 | Gupta | ................ | G06K 9/00295 |
| | | | | 382/103 |
| 2009/0192647 A1* | 7/2009 | Nishiyama | ............. | B25J 9/0003 |
| | | | | 700/215 |
| 2009/0244309 A1* | 10/2009 | Maison | .............. | G06K 9/00369 |
| | | | | 348/222.1 |
| 2009/0257621 A1* | 10/2009 | Silver | .................. | G06K 9/6202 |
| | | | | 382/103 |
| 2010/0027844 A1* | 2/2010 | Akita | ...................... | G06T 7/269 |
| | | | | 382/103 |
| 2010/0303289 A1* | 12/2010 | Polzin | ................ | G06K 9/00342 |
| | | | | 382/103 |
| 2011/0071675 A1* | 3/2011 | Wells | ................... | G06K 9/3216 |
| | | | | 700/250 |
| 2011/0293137 A1* | 12/2011 | Gurman | ............. | G06K 9/00201 |
| | | | | 382/103 |
| 2011/0311101 A1* | 12/2011 | Rafii | .................. | G06K 9/00201 |
| | | | | 382/103 |
| 2012/0025989 A1* | 2/2012 | Cuddihy | ............ | G06K 9/00369 |
| | | | | 340/573.1 |
| 2012/0092328 A1* | 4/2012 | Flaks | .................... | G02B 27/017 |
| | | | | 345/419 |
| 2012/0195471 A1* | 8/2012 | Newcombe | ............. | G06T 7/194 |
| | | | | 382/106 |
| 2012/0250978 A1* | 10/2012 | Taylor | ................ | G06K 9/00771 |
| | | | | 382/154 |
| 2012/0269384 A1* | 10/2012 | Jones | ................. | G06K 9/00201 |
| | | | | 382/103 |
| 2012/0269391 A1* | 10/2012 | Saito | ...................... | G08G 1/165 |
| | | | | 382/103 |
| 2013/0107010 A1* | 5/2013 | Hoiem | ..................... | G06K 9/46 |
| | | | | 348/47 |
| 2013/0114861 A1* | 5/2013 | Takizawa | .................. | G06T 7/74 |
| | | | | 382/106 |
| 2014/0022081 A1 | 1/2014 | Ribble et al. | | |
| 2015/0227784 A1* | 8/2015 | Roy | .................. | G06K 9/00771 |
| | | | | 382/103 |

OTHER PUBLICATIONS

Hedau, Varsha, Derek Hoiem, and David Forsyth. "Thinking inside the box: Using appearance models and context based on room geometry." European Conference on Computer Vision. Springer, Berlin, Heidelberg, 2010.*

Ni, Bingbing, Dat, Nguyen Chi, and Moulin, Pierre, "RGBD-Camera Based Get-up Event Detection for Hospital Fall Prevention", ICASSP 2012, p. 1405-1408.

Ross Girshick, et al. "Efficient Regression of General-Activity Human Poses from Depth Images"—Publication, Oct. 2011—8 pages.

Jamie Shotton, et al. "Real-Time Human Pose Recognition in Parts from a Single Depth Image"—Publication, Jun. 2011—8 pages.

Rose Johnson, et al. "Exploring the Potential for Touchless Interaction in Image Guided Interventional Radiology"—Publication, May 2011—10 pages.

Jamie Shotton, et al. "TextonBoost for Image Understanding: Multi-Class Object Recognition and Segmentation by Jointly Modeling Texture, Layout and Context"—Pub. Jan. 9.

Toby Sharp "Implementing Decision Trees and Forests on a GPU"—Publication, 2008—14 pages.

Jamie Shotton, et al. "Semantic Texton Forests for Image Categorization and Segmentation"—Publication, 2008—8 pages.

\* cited by examiner

IMAGE CAPTURE SYSTEM

CROSS-REFERENCE TO RELATED APPLICATIONS

The present application is a continuation under 35 U.S.C. § 120 of U.S. patent application Ser. No. 13/690,261, filed Nov. 30, 2012, entitled "IMAGE CAPTURE SYSTEM," which is hereby incorporated by reference in its entirety. U.S. patent application Ser. No. 13/690,261 claims the benefit under 35 U.S.C. § 119(e) of U.S. Provisional Application Ser. No. 61/565,865, entitled MOTION CAPTURE SYSTEM, filed on Dec. 1, 2011; U.S. Provisional Application Ser. No. 61/583,241, entitled IMAGE CAPTURE SYSTEM, filed on Jan. 5, 2012; U.S. Provisional Application Ser. No. 61/670,317, entitled IMAGE CAPTURE SYSTEM, filed on Jul. 11, 2012; and U.S. Provisional Application Ser. No. 61/709,354, entitled IMAGE CAPTURE SYSTEM, filed on Oct. 4, 2012. U.S. Provisional Application Ser. Nos. 61/565,865; 61/583,241; 61/670,317; and 61/709,354 are herein incorporated by reference in their entireties.

BACKGROUND

Cameras are configured to capture images within the cameras' field-of-view. Cameras may be configured to capture data representing color frame images, such as red-green-blue cameras, and/or configured to capture data representing depth frame images. In some configurations, cameras configured to capture depth frame data transmit a near-infrared light over a portion of the cameras' field-of-view and determine a time of flight associated with the transmitted light. In other implementations, the depth may be determined by projecting a structured pattern of infrared light and determining depth from an infrared camera utilizing suitable parallax techniques.

SUMMARY

A system and a computer implemented method are described that allows for the tracking of an exercise occurring within a physical environment. In one or more implementations, the system includes a depth sensing device configured to obtain depth values associated with a plurality of pixels. The depth values indicating distances from one or more physical objects in a physical environment to the depth sensing device. The system also includes a computing device in communication with the depth sensing device. The computing device includes a memory configured to store one or more modules and a processor coupled to the memory. The processor is configured to execute the one or more modules to cause the processor to: identify a point corresponding to at least one pixel representing a portion of at least one physical object within the physical environment based upon the pixel depth values; track the point through a plurality of image frames; and determine whether at least one repetition has occurred based upon the tracked point. In another implementation, the system may be configured to identify pixels as representing a body segment of a subject and track the movement of the body segment. In this implementation, the system may provide near real-time feedback to the subject and/or the subject's medical personnel.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Example Implementations

Figure 1:
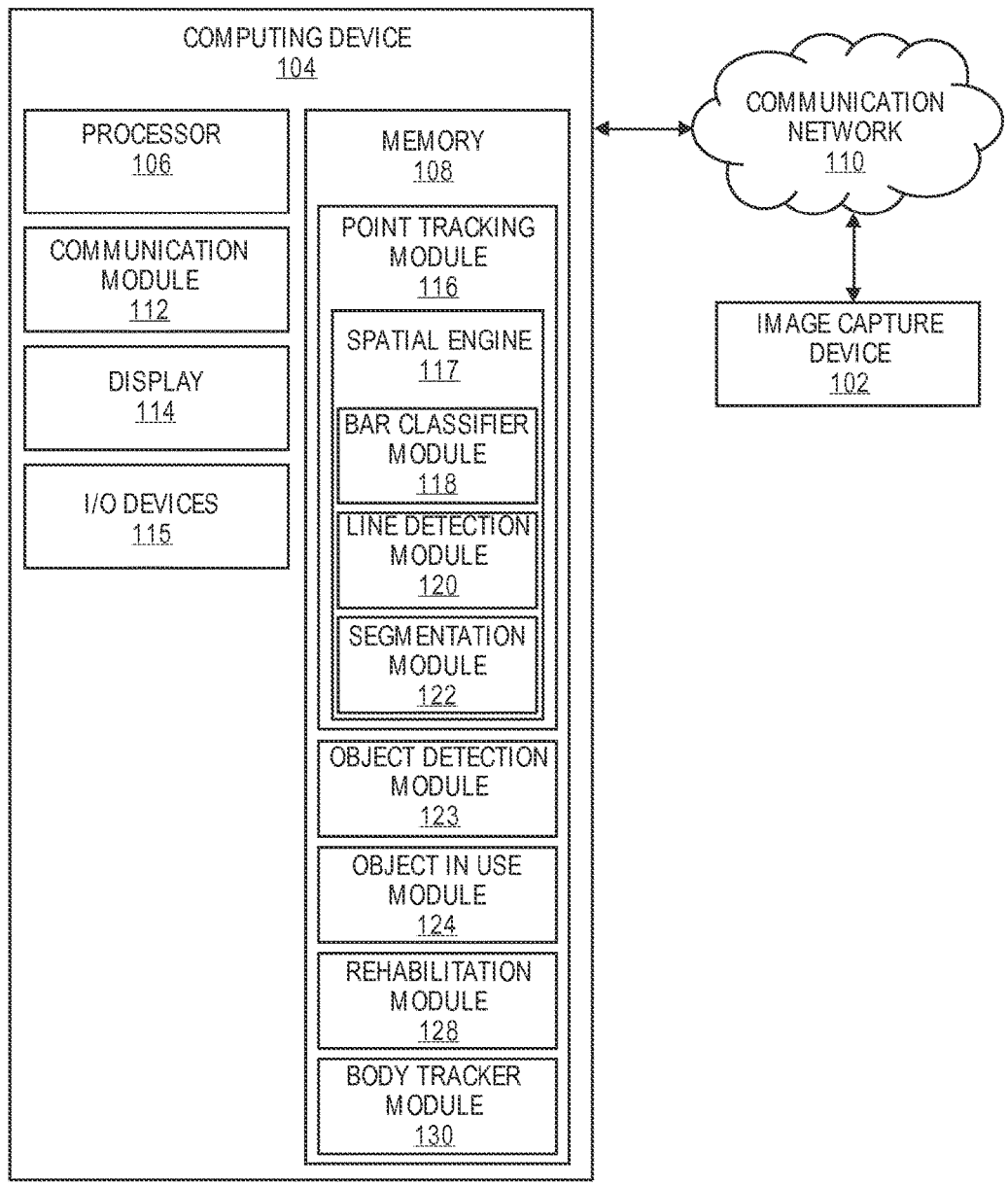
FIG. 1 is a block diagram of an image capture system in accordance with an example implementation of the present disclosure.

FIG. 1 illustrates an image capture system 100 in accordance with an example implementation of the present disclosure. As shown, the image capture system 100 includes one or more image capture devices (e.g., one or more cameras 102) and a computing device 104 communicatively coupled to the cameras 102. The cameras 102 are configured to capture images and per-pixel depth information in a field-of-view (FOV) of the cameras 102. Thus, the cameras 102 may function as depth sensing devices in some implementations. In an implementation, the cameras 102 may be depth cameras, such as Red-Green-Blue depth (RGB-D) cameras operable to capture depth frame image data representing one or more depth frame images and to capture color frame image data representing one or more color (RGB) frame images. In an embodiment, the cameras 102 may include, but are not limited to: a near infrared light configured to generate a near infrared light pattern onto the objects within the FOV, a complementary-metal-oxide-semiconductor (CMOS) sensor device configured to measure the depth of each object within the FOV, and a CMOS camera device. For example, RGB-D cameras can identify various objects within the FOV of the cameras 102 and estimate the depth of the identified objects through various depth approximation techniques. For instance, the RGB-D cameras may transmit a structured light pattern in the near-infrared spectrum and utilize suitable parallax techniques to estimate the depth of the objects within the cameras' 102 FOV in order to generate depth image data representing one or more depth frame images. Thus, the cameras 102 captures data to allow for generation of a depth frame image representing at least partially objects within the cameras' 102 FOV. The cameras 102 may also be configured to capture color frame image data representing a color frame image at least partially representing objects within the cameras' 102 FOV. In other words, the cameras 102 can refer to any camera that is capable of obtaining distance or depth information in addition to two-dimensional pixel information.

In an implementation, the cameras 102 provide the ability to capture and map three-dimensional video imagery in addition to two-dimensional video imagery. For example, the cameras 102 can capture two-dimensional data for a plurality of pixels that comprise the video image. These data values represent color values for the pixels (e.g., red, green, and blue [RGB] values for each pixel that represents the environment). Thus, objects captured by the cameras 102 can appear as two-dimensional objects via a monitor (e.g., a display, as described in greater detail herein). As mentioned above, the cameras 102 can also capture depth data within the cameras' 102 FOV. Thus, the cameras 102 are configured to capture the x and y components (e.g., x and y values) of the environment within the FOV using RGB values (captured image data, such as the color frame data representing a color frame image) for each pixel in the scene. However, the cameras 102 are configured to also capture the z-components of the environment, which represent the depth values (e.g., depth estimate data corresponding to the z-axis) within the environment.

In other words, the camera(s) 102 provide the ability to capture and map (with the processor described below) the third-dimension in addition to two-dimensional video imagery. Thus, the camera(s) 102 are configured to capture two-dimensional data for a plurality of pixels that comprise the video image. These values are color values (e.g., color frame image data) for the pixels (e.g., the RGB values for each pixel). In addition, the camera(s) 102 also capture the z-components of the scene (e.g., depth frame image data), which represent the depth values for the scene.

Figure 2A:
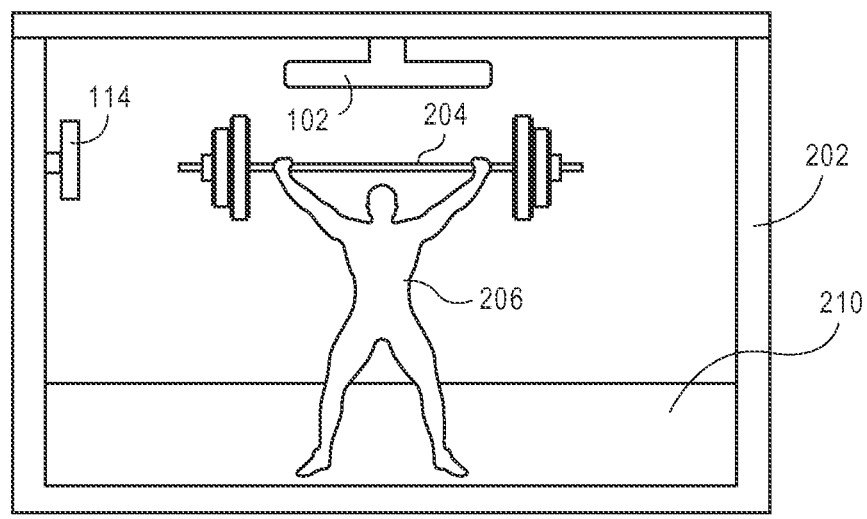
FIG. 2A is an illustration of a physical environment that includes a weight rack, a weight bar, and a subject utilizing the weight bar to perform an exercise, where the weight rack includes an image capture device to capture one or more image frames corresponding to the exercise.

The cameras 102 furnish the captured data (color frame image data, depth frame image data) to the computing device 104. In a specific implementation, the cameras 102 may be configured to capture images representing environmental views within the FOV of the cameras 102. For example, in a specific implementation, the cameras 102 may capture image data representing floor and a weight rack 202 within the FOV (see FIG. 2A). The weight rack 202 may be configured to hold a weight bar, such as the weight bar 204 shown in FIG. 2A, in position while the weight bar 204 is not in use. In other implementations, the cameras 102 may be utilized to track a subject's rehabilitation progress, as discussed in greater detail below.

The computing device 104 may be configured in a variety of ways. For example, the computing device 104 may be a server computing device, a desktop computing device, a laptop computing device, a mobile computing device, or the like. As shown in FIG. 1, the computing device 104 includes a processor 106 and a memory 108. The camera(s) 102 provides data representing the video images to the processor 106, which is configured to utilize the data as described herein.

The processor 106 provides processing functionality for the computing device 104 and may include any number of processors, micro-controllers, or other processing systems and resident or external memory for storing data and other information accessed or generated by the computing device 104. The processor 106 may execute one or more software programs (e.g., modules) that implement techniques described herein. For example, the processor 106, in conjunction with one or more modules as described herein, is configured to generate a depth mask (i.e., video image) of the environment based upon the depth estimate data (e.g., z-component data) captured by the cameras 102. For example, one or more modules are configured to cause the processor 104 to continually monitor the depth value of at least substantially all of the pixels that represent the captured environment and stores the greatest (deepest) depth value associated with each pixel. For instance, the modules cause the processor 104 to continually monitor for a pre-determined amount of time (e.g., a plurality of frames) the depth value of the pixels and stores the deepest depth value measured during the time interval. Thus, the depth mask comprises an accumulation of depth values and each value represents the deepest depth value of a pixel measured over the time interval. The processor 104 can then be instructed to generate a point cloud based upon the depth mask that includes a set of point values that represent the captured environment.

The memory 108 is an example of tangible computer-readable media that provides storage functionality to store various data associated with the operation of the computing device 104, such as the software program (a non-transitory computer-readable medium embodying a program executable by the processor 106) and code segments mentioned herein, or other data to instruct the processor 106 and other elements of the computing device 104 to perform the steps described herein.

The computing device 104 is communicatively coupled to the cameras 102 over a communication network 110 through a communication module 112 included in the computing device 104. The communication module 112 may be representative of a variety of communication components and functionality, including, but not limited to: one or more antennas; a browser; a transmitter and/or receiver; a wireless radio; data ports; software interfaces and drivers; networking interfaces; data processing components; and so forth.

The communication network 110 may comprise a variety of different types of networks and connections that are contemplated, including, but not limited to: the Internet; an intranet; a satellite network; a cellular network; a mobile data network; wired and/or wireless connections; and so forth. Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; and so on. Wired communications are also contemplated such as through universal serial bus (USB), Ethernet, serial connections, and so forth.

The computing device 104 is also communicatively coupled to a display 114 to display information to a user of the computing device 104. In embodiments, the display 114 may comprise an LCD (Liquid Crystal Diode) display, a TFT (Thin Film Transistor) LCD display, an LEP (Light Emitting Polymer) or PLED (Polymer Light Emitting Diode) display, and so forth, configured to display text and/or graphical information such as a graphical user interface. The processor 106 is configured to request depth image data and color frame image data from the cameras 102 (e.g., image capture device) and create an association between the depth image data and the color frame image data. In an implementation, the processor 106 may be configured to provide the associated data to the display 114 for display purposes. For example, the processor 106 may be configured to cause the display of video imagery that represents the captured environment at the display 114.

As shown in FIG. 1, the computing device 104 is also communicatively coupled to one or more input/output (I/O) devices 115 (e.g., a keypad, buttons, a wireless input device, a thumbwheel input device, a trackstick input device, a touchscreen, and so on). The I/O devices 115 may include one or more audio I/O devices, such as a microphone, speakers, and so on.

Example Bar Tracking Implementation

Figure 2B:
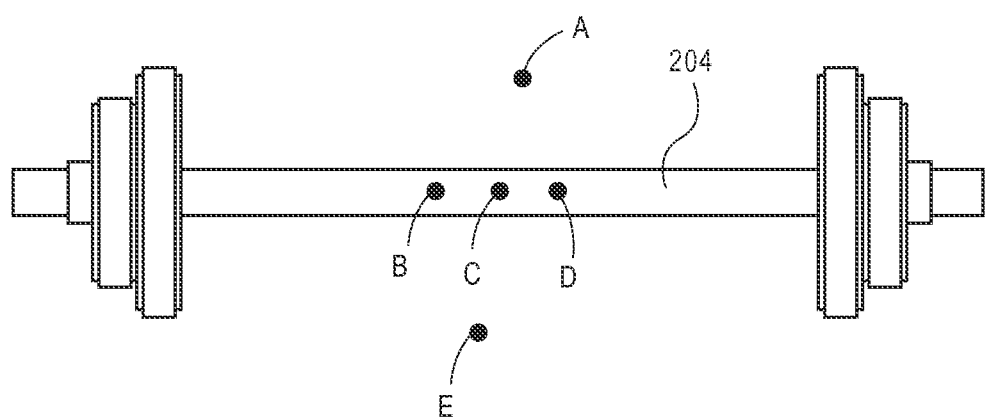
FIG. 2B illustrates a depth value (z-value) image frame including a plurality of pixels that represent the weight bar.

The computing device 104 includes a point tracking module 116, which is storable in memory 108 and executable by the processor 106. The point tracking module 116 is representative of functionality to classify a point within one or more frame images (e.g., depth frame images, color frame images) captured by the cameras 102. For example, the point tracking module 116 receives data representing the frame images from the cameras 102 and classifies pixels of the frame images as representing the object or not representing the object. In a specific implementation, the object may comprise the weight bar 204 shown in FIGS. 2A and 2B. The point tracking module 116 then generates a point to correspond to the classified pixels for tracking purposes. The classified point may represent an object captured within the FOV of the cameras 102, and the point may be utilized to track data (e.g., repetitions, etc.) relating to an object, such as exercise equipment or the like. For example, the point tracking module 116 may be configured to classify a point representing a weight bar based upon an association between the color frame image and the depth frame image.

As shown in FIG. 1, the point tracking module 116 includes a spatial engine 117. The spatial engine 117 is configured to instantiate one or more modules (described below) that are configured to classify a point (or points) representing a weight bar (e.g., weight bar 204 shown in FIG. 2A) within one or more captured frames. Thus, once the spatial engine 117 instantiates the modules, the modules utilize data representing the captured environment (e.g., image data representing the weight rack, image data representing the floor, image data representing the weight bar, etc.) to classify pixels and generate a point representing an object (e.g., the weight bar) in successive frames. The object may be at least partially represented within the frame images (represented by one or more pixels). The point may be utilized to generate and track data relating to the item captured within the FOV. For example, the point may be utilized to generate and track data (e.g., repetitions, velocity of the repetition, etc.) relating to a user using the weight bar.

As shown in FIG. 1, the spatial engine 117 includes a bar classifier module 118, a line detection module 120, and a segmentation module 122. The modules 118, 120, 122 are configured to receive image data from the cameras 102 and parameters (or coefficients) from a user interface (e.g., communication module 112, I/O devices 115, etc.) relating to a specific exercise type. In a specific implementation, the parameters may indicate a specific lift exercise type (e.g., squat, bench press, hang clean, etc.). In an implementation, the spatial engine 117 may utilize the parameters to determine a combination of modules 118, 120, 122 to classify a point to represent an object within the FOV. In another implementation, the spatial engine 117 may utilize the parameters to determine which module 118, 120, 122 is used to classify a point to represent an object within the FOV. It is contemplated that a specific module 118, 120, 122, or combination of modules, may be better suited to classify a point depending upon the type of exercise occurring and the request provided by the point tracking module 116. For example, the bar classifier module 118 may be better suited to classify a point representing the weight bar when a bench press is occurring within the FOV of the cameras 102.

The bar classifier module 118, which is storable in memory 108 and executable by the processor 106, is representative of functionality to classify each depth frame pixel (e.g., based upon the z-value of the pixels) as potentially corresponding to (e.g., representing) a bar (e.g., a per pixel bar classifier) within the captured FOV. In a specific example, a user in the cameras' 102 FOV may be utilizing a weight bar 204 for exercising and/or rehabilitation. In this example, the bar classifier module 118 is configured to classify (e.g., an outward classifier) each pixel within the depth frame image as representing the bar 204 or not representing the bar 204 (e.g., in a specific example, each pixel is classified as representing the weight bar 204 [see FIG. 2B] or classified as not representing the weight bar 204). The bar classifier module 118 is configured to classify each pixel by identifying (e.g., selecting) a starting point (a starting pixel [starting point "C" illustrated in FIG. 2B]) within the depth frame image (e.g., an outward classifier). The module 118 then identifies four (4) depth-variant offset points (pixels) within at least a portion of the depth frame image. For example, the module 118 may only identify (e.g., select) offset points within an at least partially segmented depth frame image (e.g., analyze the points comprising the largest segment in the scene). In another example, the module 118 may only identify offset points within a specified region within the depth frame image. In some instances, by only analyzing a portion of the depth frame image, the number of falsely identified pixels (points) may be reduced. The offset points are represented as points "A," "B," "D," and "E" in FIG. 2B. Two (2) points, of the four (4) offset points, are identified (points "B" and "D") that are at least substantially equidistant and at least substantially collinear with the starting point (point "C"). The module 118 then determines whether the remaining offset points (points "A" and "E") are zero (i.e., infinite distance) and whether "B" and "D" are not zero (and within an acceptable distance from the cameras 102 relative to point "C"), the starting pixel (point "C") is classified as representing the weight bar 204 within the depth frame image. In an implementation, the module 118 may be configured to return a zero for any pixels not belonging to the object. The distance values between the various classified points may be input to a mean shift algorithm to identify approximately the position of the center point and remove identified outliers, and the resultant is utilized to track the weight bar 204. Thus, the classified center point of the bar 204 (e.g., select point "C" as point, or pixel, to track) in the image may be used to represent the weight bar 204's location for tracking purposes (e.g., track the point through successive image frames). The module 118 may also fit a line to the points along the pixels classified as representing the weight bar 204 (overlay a line extending along points "B" to "D"). For example, the bar classifier module 118 may utilize offset data (as described herein) to generate (e.g., apply) a line to represent the weight bar 204 displayed within a display 114.

Additionally, the module 118 is configured to classify whether a pixel represents the weight bar through a downward classifier. More specifically, the module 118 causes the processor 106 to determine the depth of the vertical line segments above and below (e.g., segments of one or more pixels oriented above or below) the selected pixel (e.g., selected point "C"). If the selected pixel represents the object, the pixels above and below the selected pixel may have a depth value that is significantly higher (e.g., greater z-component) as compared to the depth value of the selected pixel rather than a significantly lower depth value. If the processor 106 determines that the plurality of pixels above and/or below the selected pixel have corresponding depth values that are significantly higher than the depth value of the selected pixel, the processor 106 moves to determining the depth of the horizontal line segments. The module 118 also causes the processor 106 to determine the depth of the horizontal line segments (e.g., plurality of pixels) to the left and the right of the selected pixel. The length (e.g., number of pixels) tested (e.g., depth determination) are determined by the depth of the selected pixel. Based upon the depth determination of the horizontal line segments, the depth of the horizontal line segment (e.g., depth values for the plurality of pixels within the horizontal line segment) should be at least substantially (e.g., within ten percent (10%) of) the same depth of as the depth of the selected pixel. It is understood that the module 118 may permit the processor 106 to continue depth determination when a certain percent (e.g., between one to five percent (1 to 5%)) of depth information within the horizontal line segment is missing. Thus, if the processor 106 determines that the vertical line segments have a depth significantly higher than the depth value of the selected pixel and that the horizontal line segments have a depth value that is at least substantially the same as the depth value of the selected pixel, the processor 106 is instructed to classify the pixel as belonging to the object.

The bar classifier module 118 may also utilize other types of analysis (or in combination with the analysis described above) and may be utilized to identify, classify, and track the weight bar 204 as well. For example, the bar classifier module 118 may be configured to examine a predetermined range of neighboring pixels (e.g., pixels that are positioned above, below, and centered with the pixel of interest). Thus, the module 118 may identify a pixel for classification and examine the pixels surrounding (and proximal to) the identified pixel for classification of the identified pixel. In another example, the module 118 may identify the hue of the pixels representing the weight bar 204 (e.g., weight bar 204 has a consistent hue to allow for identification and tracking purposes), marks included on the weight bar 204, and so forth.

Figure 4:
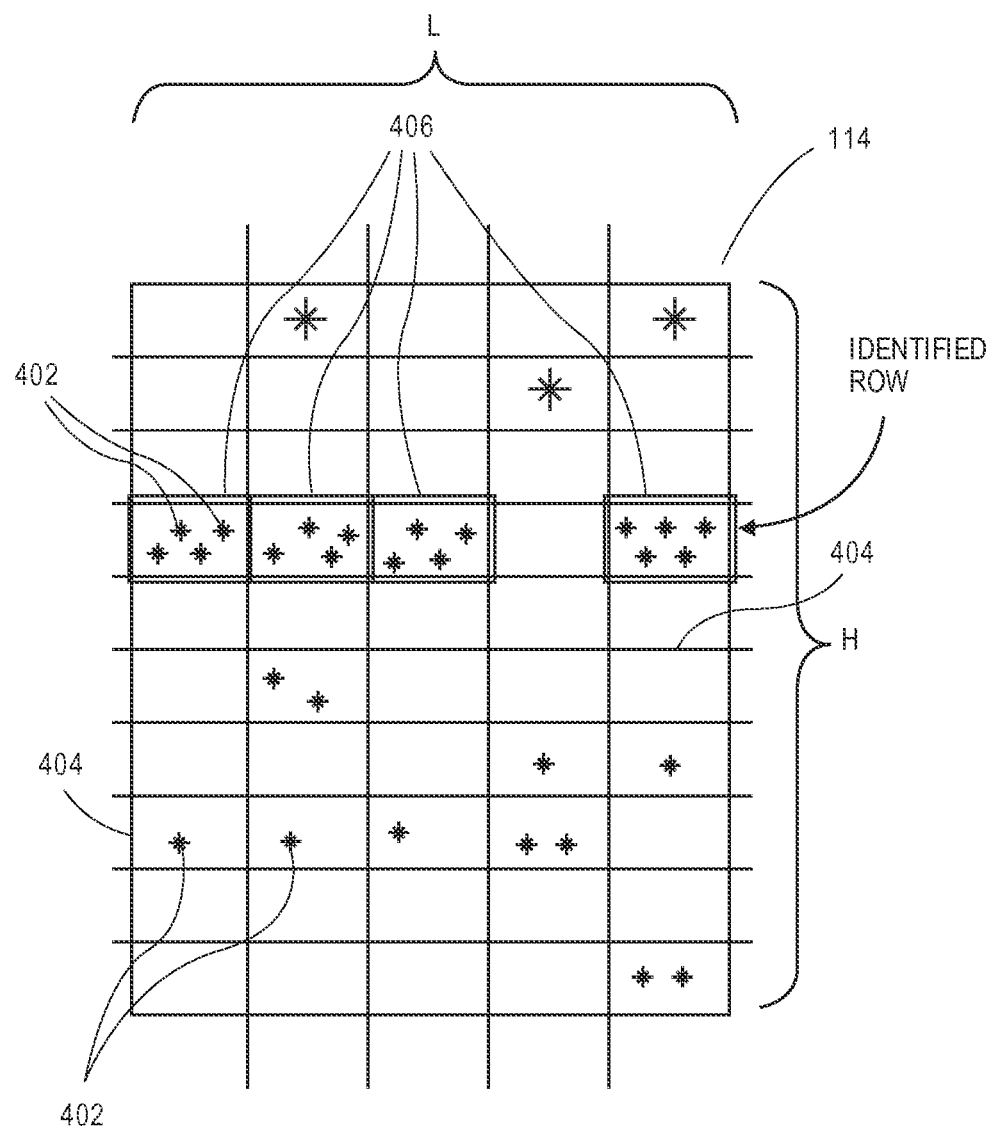
FIG. 4 illustrates an example color frame image that is grouped into rectangular regions, where each asterisk represents an identified in-motion pixel.

The line detection module 120, which is storable in memory 108 and executable by the processor 106, evaluates (e.g., through a Hough transform, RANSAC, or the like) in-motion color frame image data captured by the cameras 102 to identify at least a portion of in-motion color frame image pixels as representing the object (e.g., weight bar 204). In an implementation, the line detection module 120 utilizes a Hough transform to identify a subset of in-motion color frame image pixels that most-likely represent the weight bar 204. For example, the line detection module 120 analyzes the brightest (e.g., most intense) color frame image pixels in motion. Thus, the module 120 may utilize the Hough transform to identify pixels having a greater intensity (as compared to neighboring pixels) and that are nearly horizontal lines among the pixels whose intensities have changed at least significantly since the previous frame. In an implementation, the line detection module 120 divides a current color frame image into a number of evenly-sized rectangular regions that are utilized by the Hough transform. Each rectangular region represents a distinct subset of the current color frame image. For instance, as shown in FIG. 4, the module 120 is configured to group, or collect, in-motion pixels 402 (represented as asterisks in FIG. 4) into evenly-sized rectangular regions 404 (e.g., a 2×10 grid of pixels) correlated to a portion of the current color frame image (e.g., the module 120 identifies horizontal (non-vertical) strips (e.g., rows) 406 of in-motion pixels 402). The module 120 maintains the in-motion pixels 402 if a predefined minimum pixel threshold (e.g., approximately ninety percent [90%] of the pixels) within the rectangular region 404 are identified as in-motion pixels. The module 120 then removes at least substantially all of the pixels not identified as within the rectangular regions 404 that have surpassed the minimum pixel threshold. The module 120 then utilizes a Hough transform to generate a bar line in color that represents the object (weight bar 204) based upon the modified image (e.g., the image containing the in-motion pixels). For instance, the module 120 may utilize the Hough transform to locate collinear points (pixels) within the modified image. This approach may assist in removing one or more false lines from the color frame image(s) so only the desired object is identified and represented by the bar line. In a specific embodiment, a frame difference operator (e.g., subroutine) may identify in-motion pixels for the line detection module 120 (e.g., comparing each pixel of a current frame image with the respective pixel of the previous frame image, or the like). In another implementation, the module 120 may reject the generated bar line (generated via the Hough transform) if the generated bar line does not intersect (e.g., cross) one or more pixels identified as representing the user. The one or more pixels that represent the user may be identified utilizing the segmentation module 122, as described herein. The modules 118, 120 are configured to cause the processor 106 to "re-fit" the line identified through the in-motion color frame image data (RGB) process. Thus, as described above, the module 118 may have caused the classification of one or more pixels as representing the weight bar 204 (as well as fit a line to those classified pixels), and the module 120 may have caused the classification of one or more pixels as representing the weight bar 204 (as well as fit a line to those classified pixels). The module 120 may then cause the processor 106 to re-fit a line to the RGB pixels that have been classified as belonging to the weight bar 204 based upon the depth information. For example, the module 120 may cause the processor 106 to attempt to fit a line to corresponding color frame image pixels based the depth frame image pixels. If this re-fit requires the line to be adjusted beyond a certain pre-defined threshold (in the color frame images) to match the corresponding depth pixels, the module 120 causes the re-fit line to be rejected.

The segmentation module 122, which is storable in memory 108 and executable by the processor 106, is configured to remove non-essential pixels (e.g., pixels identified as not representing the object) and/or noise with the depth frame images. For example, the point tracking module 116 and the spatial engine 117 may be configured to only identify pixels associated with the object and not pixels associated with the background of the frame image. For example, due to the nature of a squat exercise, a weight bar 204 may be partially obstructed by a person's 206 head. The partial obstruction may impede the classification of pixels by the bar classifier module 118 and/or the line detection module 120. Thus, the segmentation module 122 may be configured to classify a point representing a portion of the person's head to assist with tracking of the weight bar (e.g., weight bar 204). In an implementation, the segmentation module 122 may identify a portion of the person's head utilizing the depth frame pixels and generate a point representing a portion of the person's head via a suitable mean shift algorithm, or the like. While the person within the FOV is engaged in a squat exercise, the segmentation module 122 may continuously classify pixels within successive depth frame images as representing a portion of the person's head, and the points may be utilized to track repetitions relating to the squat exercise.

The computing device 104 also includes an object detection module 123, which is storable in memory 108 and executable by the processor 106, which is representative of functionality to determine a floor within the FOV of the cameras 102. The module 123 is configured to cause the processor 106 to identify pixels representing the floor 210 (see FIG. 2A). In an implementation, the processor 106 randomly selects a number of regions (e.g., subset of pixels) within the depth frame. The regions may be of varying size in specific examples. From those selected regions, the processor 106 randomly selects (identifies) a number of pixels, and from those pixels, the processor 106 identifies the pixels having the greatest z-component value (e.g., pixels representing an object that is most distant from the camera as these are initially considered as pixels most likely representing the floor). With these identified pixels, the processor 106 utilizes a RANSAC processor to determine a best-fit three-dimensional plane for the identified pixels. This best-fit plane is compared against a pre-defined model plane of the floor (e.g., comparison may be the dot product between the two planes' normal vectors). If the scalar result of the dot product (comparison) is within a pre-defined acceptable range, the identified three-dimensional plane represents the floor. Based upon the analysis, the processor 106 is configured to generate a three-dimensional plane equation that represents the floor within the FOV. The equation may be stored in the memory 108 to allow for retrieval during later uses of the system 100.

The module 123 is configured to cause the processor 106 to identify an active region that represents the floor plane. For example, the active region identifies the bounds of the floor plane. Thus, the processor 106 is configured to identify activity occurring within the active region (e.g., pixels representing an activity having x, y, and z components outside of the active region are not identified by the processor 106). In other words, objects and/or activity not within the active region are ignored (e.g., defined as "not in the trackable area").

In one or more implementations, the object detection module 123 is further configured to determine the pixel representing the weight rack 202 during initialization of the system 100. For example, during initialization of the system 100 (e.g., before any objects or exercises are performed within the active region), the module 123 is configured to cause identification of the weight rack 202 within the FOV. Thus, the processor 106 is configured to identify pixels (based upon x, y, and z components of the pixels) as representing the weight rack 202 or not representing the weight rack 202. For instance, the weight rack 202 may be identified based upon the characteristics of the weight rack 202 (e.g., pixels having z-components closer to the camera as compared to pixels representing the wall, pixels arranged in a generally linear configuration, etc.). Once the weight rack 202 pixels have been identified, a mask may be applied to subsequent depth frames during operation of the system 100 (e.g., depth frames where exercises are being performed, etc.) to remove the data that represents the weight rack. Thus, depth frame images are generated that include at least substantially no depth frame image data that represent the weight rack.

The computing device 104 includes an object in use module 124, which is storable in memory 108 and executable by the processor 106. The object in use module 124 is representative of functionality to determine whether the weight bar 204 is in use (e.g., weight bar is positioned within a weight rack). The object in use module 124 utilizes data representing an environment within the FOV. For example, the module 124 may utilize image data (e.g., color frame image data, depth frame image data, combinations thereof) representing the weight rack to determine whether a weight bar 204 is not in use (e.g., the weight bar is positioned within the weight rack). In a specific implementation, the module 124 may first determine the relative position of weight rack 202 within the captured frame or frames. Once the relative position is defined, the object in use module 124 may then define a buffer region proximate (e.g., adjacent, etc.) to the position of the weight rack 202. As the image data is provided to the module 124, the module 124 determines whether the relative position of the weight bar 204 (as represented by the image data) is within the buffer region. The module 124 may determine that the weight bar 204 is no longer in use when the relative position of the weight bar 204 (e.g., pixels representing the weight bar) is within the buffer region for a predetermined time (e.g., a predetermined amount of successive frames captured by the cameras 102). If the module 124 determines the weight bar 204 to be no longer in use, the point tracking module 116 may not utilize the classified pixels for tracking and monitoring purposes.

As shown in FIG. 1, the computing device 104 also includes a tracking module 126, which is storable in memory 108 and executable by the processor 106. The tracking module 126 utilizes the data generated by the bar classifier module 118, the line detection module 120, and/or the segmentation module 122 to determine and track the number of repetitions that occurred within the FOV of the cameras 102. For example, the tracking module 126 may utilize the data provided by the bar classifier module 118, the line detection module 120, and/or the segmentation module 122 to determine the number of repetitions a user of a weight bar 204 within the FOV has executed, as well as the velocity and/or acceleration of the weight bar 204 during various defined intervals (e.g., a single repetition, mean average over multiple repetitions, etc.).

The tracking module 126 utilizes the datasets (e.g., classified pixels, etc.) generated by the point tracking module 116 to determine statistics associated with the object being tracked (e.g., weight bar 204) within the FOV during each cameras 102 capture event (e.g., each time the cameras 102 captures data representing the depth frame image and data representing the color frame image). In a specific implementation, the tracking module 126 receives a point from the point tracking module 116 to determine an approximate position of the represented object within the FOV during each cameras 102 capture event. The tracking module 126 may utilize the datasets generated by the object detection module 123 to determine a relative position of the representative point (point "C") with respect to the floor. Then, the tracking module 126 may determine that a repetition has occurred by tracking a representative point (e.g., point "C") through a number of frame images. In an implementation, the module 126 may declare a repetition has occurred when (1) the representative point (which may be computed from the line determined by the Hough transform and the pixels identified by the bar classifier module 118) has moved in subsequent frames between a predetermined minimum distance and a predetermined maximum distance; and (2) the representative point has a predetermined velocity attribute between a predetermined minimum velocity and a predetermined maximum velocity. In another implementation, the module 126 may utilize other characteristics of motion to determine statistics associated with the tracked object. For example, the module 126 may determine a horizontal displacement of the object.

The tracking module 126 may be configured to determine the velocity and/or acceleration attributes of the weight bar 204 by comparing the respective positions of the representative point throughout a pre-determined amount of frames (generated from the data sets corresponding to the depth frame image and the color frame image) utilizing the known cameras 102 capture configurations (e.g., the cameras' frames per second, etc.). The track module 126 may cause the processor 106 to determine the velocity associated with the object by determining the change in distance for the tracked position between a first frame and a second frame and dividing the positional value by the change in time between the first frame and the second frame. Thus, the velocity and/or acceleration may be approximated on a per repetition basis, a multiple repetition basis, and so forth. Additionally, the tracking module 126 may utilize the data generated from the object detection module 123 to determine the relative position of the weight bar within the captured frame. For instance, the tracking module 126 may utilize the floor data object to determine a relative position (e.g., height) of the point representing the weight bar within the captured frame image by comparing the data representing the point to the data representing the floor.

Figure 2C:
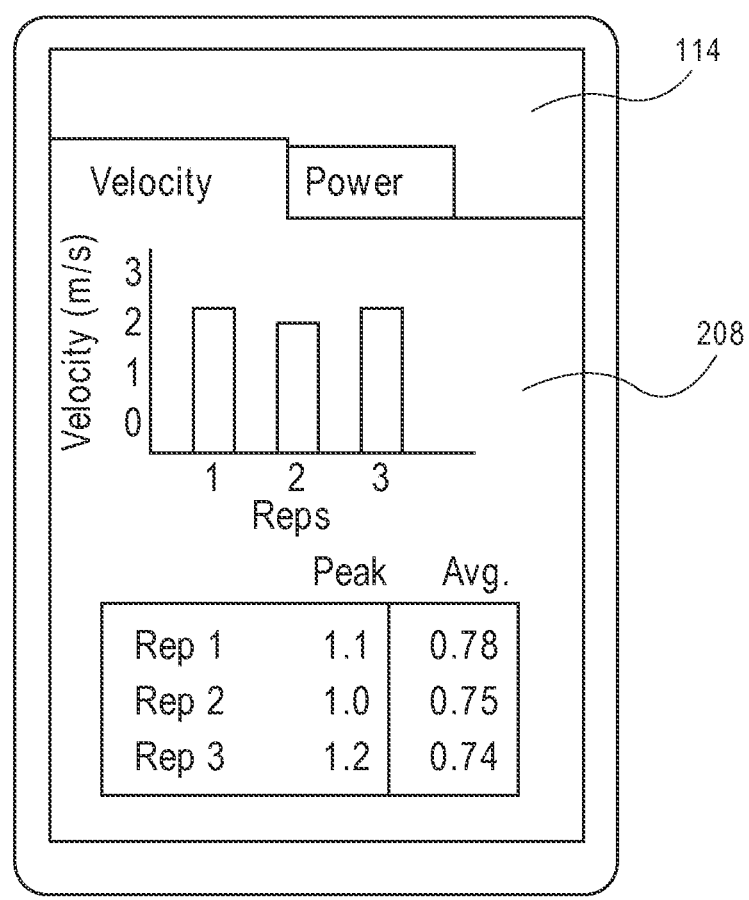
FIG. 2C illustrates a graphical representation of feedback the image capture system is configured to provide based upon the performance of the exercise.

In one or more implementations, the processor 106 may initiate instructions to cause the display 114 to display one or more images (e.g., a depth frame image, a color frame image, an image represented by both the data sets corresponding to the depth frame image and the data sets corresponding to the color frame image). The displayed images may also include the points representing the respective objects (e.g., weight bar, portion of the person's head, etc.) and/or a line overlay representing the weight bar 204. Moreover, the results (e.g., repetition, velocity, acceleration) may be displayed by the display 114, stored in memory 108 for future utilization, and so forth. In another implementation, as shown in FIG. 2C, the point tracking module 116 may be configured to cause display of one or more graphical representations 208 related to the tracked data associated with the exercise. For instance, the graphical representations may convey the velocity associated with weight bar for athletes, which may correlate to an athlete's exercise performance. The graphical representations 208 may also convey an athlete's exercise performance (e.g., velocity associated with a squat exercise performance) over a predetermined time period.

While the present disclosure describes one specific example (e.g., identifying a weight bar 204), it is contemplated that the present disclosure may be utilized in other settings as well. For example, the present disclosure may be utilized to identify a medical/rehabilitation apparatus within a medical/rehabilitation setting, and so forth.

Example Pixel Classification Process

Figure 3:
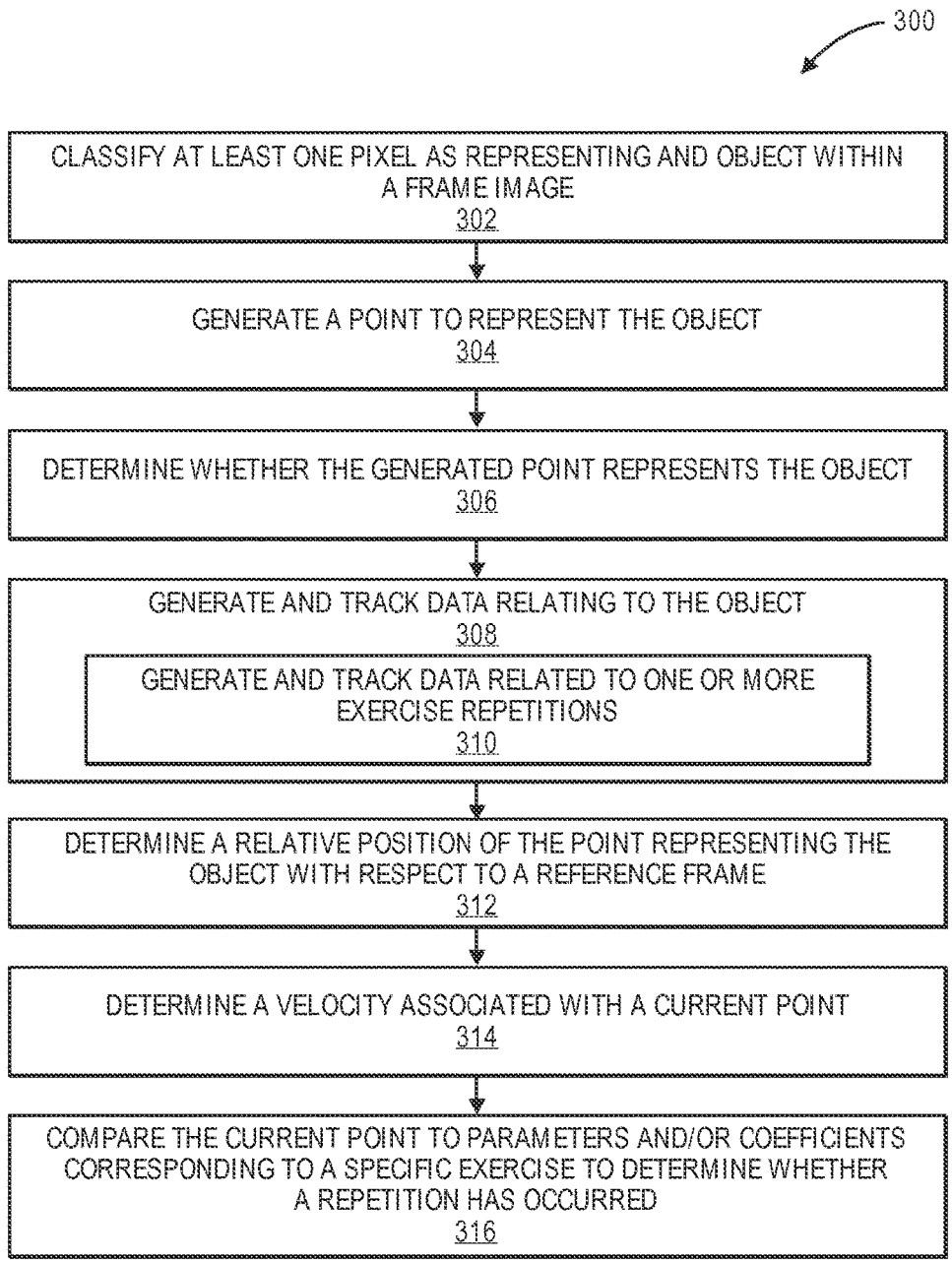
FIG. 3 is a flow diagram illustrating an example process for classifying and tracking pixels in accordance with the present disclosure.

FIG. 3 illustrates an example process 300 for generating points within a captured frame image to represent an object captured within the FOV of the cameras 102 and determining whether the object is in use. The points may be utilized to measure and track information relating to the object (e.g., tracking repetitions of a weight bar, etc.) As shown in FIG. 3, at least one pixel (or a plurality of pixels) is classified as representing an object within a frame image (Block 302). As described above, the cameras 102 are configured to capture image data representing one or more frames within a FOV of the cameras 102 (e.g., data representing one or more color frame images, data representing one or more depth frame images). Once captured, the data is furnished to the computing device 104 to allow the point tracking module 116 to classify whether the pixels represent an object (e.g., a weight bar 204) within the one or more frame images (e.g., one or more frames that comprise the video imagery). The object may be at least partially represented within one or more frame images (e.g., the object is represented at least partially by depth frame pixels and represented at least partially by color frame pixels, etc.). In an implementation, the point tracking module 116 utilizes the parameters and/or coefficients relating to the type of exercise that a person 206 may perform within the FOV of the cameras 102 to determine which module (bar classifier module 118, line detection module 120, segmentation module 122), or combination of modules, is suited to generate a point representing the object. The tracking module 126 may then utilize the point to track the number of repetitions associated with the object.

Based upon the classification of the pixel, a point (e.g., a representative point) is generated to represent the object (Block 304). As described above, the point tracking module 116 generates a representative point (e.g., point "C" in FIG. 2B) to represent the object within the frame image. As shown in FIG. 3, a determination is made whether the generated point represents the object upon a failure to generate a point utilizing current frame image data (Block 306). For example, previous frame image data may be utilized to generate and maintain an offset dataset to assist in determining whether the generated point represents the object when the point tracker module 116 failed to generate a point (e.g., due to object being too close to a user's body, etc.). For example, the offset dataset may be utilized to extrapolate whether the current generated point is within an acceptable range of values based upon the offset dataset. In another example, the offset dataset may comprise prior relative positional data of the classified pixels (e.g., relative position of the classified pixels within the previous frame images). Thus, when the point tracking module 116 is tracking a person during a bench press exercise, the point tracking module 116 may utilize the prior positional data of the classified pixels to extrapolate a current relative position of the weight bar 204 within the frame image and continue tracking the object. In another implementation, the offset dataset may be a function of previously generated points that represented the object in previous frame images. Additionally, in the event of failure to identify a point, one or more suitable filters may be utilized in approaching a best-possible guess as to the location of the tracked point. For example, the filters may include, but are not limited to a Kalman filter, a Particle filter, and so forth. Thus, the tracking may be recovered from lost points by causing the processor 106 to estimate the most likely position of the point.

The point may be utilized to generate and to track data relating to the object (Block 308). Specifically, as shown in FIG. 3, the point may be utilized to generate data and to track the generated data related to exercise repetitions (Block 310). In an implementation, the tracking module 126 utilizes the data generated and furnished by the point tracking module 116 (e.g., the bar classifier module 118, the line detection module 120, and/or the segmentation module 122) to determine and to track the number of repetitions that occurred within the FOV of the cameras 102.

As shown in FIG. 3, a determination is made of a relative position of the point representing the object with respect to a reference plane (Block 312). In an implementation, the tracking module 126 may utilize the floor object data to determine the relative position (e.g., height) of the point representing the object with respect to the reference plane (e.g., the generated floor, which represents the floor 210, as represented by suitable three-dimensional (3D) mapping techniques). The tracking module 126 maintains the points representing the repetitions for comparison purposes. In a specific implementation, the tracking module 126 may utilize the points to determine local extrema within the context of the exercise. For example, the tracking module 126 may utilize parameters and/or coefficients relating to specific exercise to determine acceptable ranges for local minimum points and/or local maximum points. In an implementation, the parameters and/or coefficients may be stored from previous repetitions. The local minimum and maximum points are utilized by the tracking module 126 to determine whether a repetition has occurred. Once the tracking module 126 determines a repetition has occurred, the module 126 stores the repetition data and furnishes the repetition data through an application programming interface (API). The tracking module 126 then awaits data corresponding to the next repetition.

The tracking module 126 may utilize multiple techniques to determine whether the current point (e.g., point representing the weight bar within the current frame image) may be a result of noise or whether the current point represents a local minimum/maximum value. The current repetition point can be compared to previous points within a predetermined number of previous frame images (e.g., compare the current point to the each point occurring within the previous two frame images). If the current point is a local minimum/maximum point, the tracking module 126 may maintain the current point. If the current repetition data point is not a local minimum/maximum point, the tracking module 126 may classify the current point as noise. However, the repetition points not classified as a local minimum/maximum point may be maintained for later statistical analysis.

As shown in FIG. 3, a velocity associated with a current point is determined (Block 314). For example, the tracking module 126 is configured to cause the determination of the instantaneous velocity of the current point as compared to the previous frame's point. For example, the tracking module 126 may cause the processor 106 to determine the instantaneous velocity of a point that represents a local minimum/maximum value. If the instantaneous velocity associated with the current repetition point is greater than a predetermined value (e.g., ten (10) meters per second, etc.), the current point may be discarded as noise. It is contemplated that the instantaneous velocity may vary as a function of the exercise.

The tracking module 126 may also be configured to cause determination of whether the point has reached a relative minimum height with respect to the generated floor. If the minimum height has not been reached, the tracking module 126 can continue tracking the points as a current repetition. Otherwise, the tracking module 126 determines a repetition has occurred, determines velocity data corresponding to the repetition, stores the repetition data, and awaits data corresponding to the next repetition. In one or more implementations, the minimum height may be determined from configuration data (e.g., parameters, coefficients, etc.) or previous repetition data associated with the same exercise.

The tracking module 126 may also be configured to fit a parabola to one or more points representing the repetition. In an implementation, the tracking module 126 utilizes the parabola to determine local minimum/maximum points for further determination of whether a repetition has occurred.

The point (e.g., current representative point) may also be compared to other parameters and/or coefficients corresponding to a specified exercise to determine whether a repetition has occurred (Block 316). For example, the tracking module 126 is configured to utilize parameters and/or coefficients corresponding to a specified exercise to determine whether a repetition has occurred. The parameters and/or coefficients may include an acceptable range of values (e.g., an acceptable range of minimum values, an acceptable range of maximum values, etc.) that the tracking module 126 utilizes to determine whether a repetition has occurred. The parameters/coefficients may be based upon previously tracked datasets corresponding to the specified exercise, predetermined parameters/coefficients associated with a specified exercise, and so forth. Thus, the tracking module 126 may determine a repetition has occurred when at least a portion of the current repetition dataset (e.g., cumulative dataset of points representing positions of the weight bar in two or more successive frame images) occurs within the acceptable range. Moreover, the tracking module 126 may maintain parameters or coefficients corresponding to previous repetitions of the specific exercise. For example, the tracking module 126 may compare the current repetition dataset to the one or more previous repetition datasets to determine whether a repetition has occurred due to a portion of the current repetition dataset occurring within the acceptable ranges of local maximum/minimum values.

Example Rehabilitation Tracker Implementation

Figure 5A:
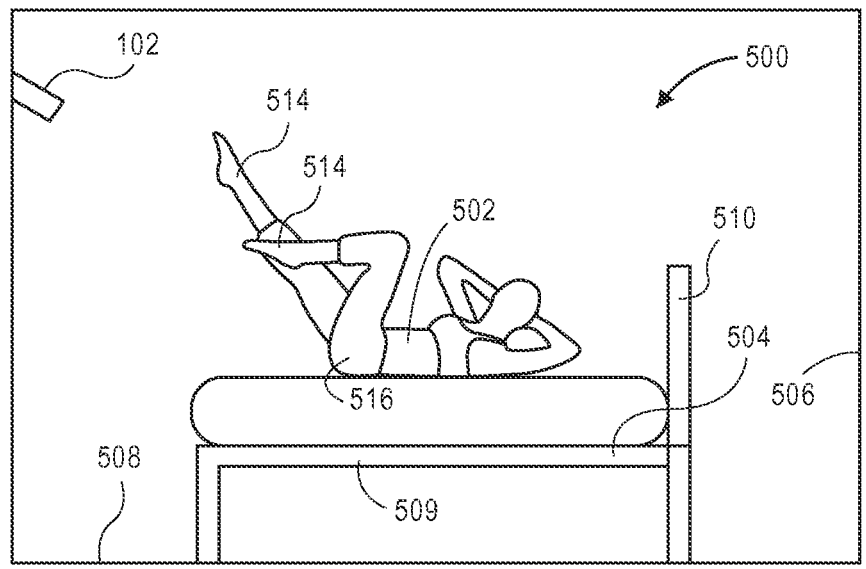
FIG. 5A is an illustration of another physical environment that includes a bed, a subject laying in the bed performing an exercise, and an image capture device positioned to capture one or more image frames corresponding to the exercise.

In one or more implementations the system 100 may be utilized to track a subject's (patient's) 502 rehabilitation (see FIG. 5A). For example, the cameras 102 may be positioned proximate to a bed 504 the subject 502 uses. The subject's regimen may include one or more rehabilitation exercises. Thus, the image capture system 100 may be utilized to track the subject's progress. As shown in FIG. 1, the computing device 104 includes a rehabilitation module 128 that is storable in memory 108 and executable by the processor 106. As described below, the module 128 is configured to cause the processor 106 to detect and monitor a subject's rehabilitation exercise occurring with the FOV of the cameras 102.

The rehabilitation module 128 is configured to cause the processor 106 to identify pixels representing the floor 508 and pixels representing the wall 506. In one or more implementations, the module 128 utilizes an iterative Random Sample Consensus (RANSAC) method (e.g., an algorithm) to define (identify) pixels that represent the floor and pixels that represent the wall. Thus, the module 128 may cause the processor 106 to initially scan the pixels and define a portion of the pixels as representing the floor and another portion of the pixels as representing the wall. The module 128 may then cause the processor 106 to further define (e.g., iteratively define) other pixels that represent the floor 508 and/or the wall 506. Additionally, the module 128 may employ a pseudo-RANSAC method where the module 128 utilizes pre-defined parameters to select pixels having values (e.g., x, y, z values) within the pre-defined parameters. In other words, the processor 106 selects pixels having values within the pre-defined parameters before the processor 106 utilizes the RANSAC method to identify whether the pixel represents the wall 506 or the floor 508 (or the pixel does not represent either the floor or the wall).

Once the pixels representing the floor 508 and the pixels representing the wall 506 have been identified, the pixels representing the bed 504 are identified. The module 128 is configured to cause the processor 106 to generate a depth mask (image) representing the environment 500 as described above. Based upon the depth mask, the module 128 is configured to cause the processor 106 to generate a point cloud representing the environment 500. In an implementation, the module 128 is configured to cause the processor 106 to identify pixels representing the bed within the depth mask. The processor 106 may be instructed to scan the depth mask in a first direction (e.g., left to right with respect to the orientation of the cameras 102, right to left with respect to the orientation of the cameras 102). Then the processor 106 may be instructed to identify pixels having a predetermined gradient change (change is z-value with respect to the adjacent pixels (e.g., pixels representing the bed have a closer z-value as compared to pixels representing the wall and/or the floor)). For example, the processor 106 compares the pixels in a left to right orientation to determine the pixels representing the bed. For instance, the processor 106 is configured to compare the z-components of the pixels within the depth mask to the z-components of the adjacent pixels to identify portions of the bed 504 (bed plane, etc.). Thus, the processor 106 is configured to identify pixels having a z-component that are closer to the cameras 102, and within a predefined gradient change, as compared to the z-component of the floor/wall pixels are identified as bed pixels.

The pixels representing the edge 509 of the bed 504 may be then extracted (identified) by utilizing one or more suitable processes to define the edges 509 of the bed 504. For example, the processor 106 may incorporate a Hough line transformation process to define the edges 509 of the bed 504. In this example, the processor 106 may detect (identify) multiple Hough lines among the potential-edge-of-bed pixels. The module 128 is configured to cause the processor 106 to select the lines that most likely correspond, or represent, to the edges 509 of the bed 504. For example, the processor 106 may identify an edge 509 of the bed 504 based upon a minimum number of pixels within the line, location (position) of the pixels toward the center of the image, a line of pixels that are spaced approximately the width of the bed, and the like. The baseboard 510 of the bed 504 may then be identified. For example, the processor 106 may scan the depth mask in a first direction (left to right) and in a second direction (down to up with respect to orientation the cameras 102) to identify pixels having z-components that are proximal (near) to the cameras 102 as compared to the z-components of wall/floor. The module 128 is then configured to cause the processor 106 to fit a polygon (active region) to the pixels representing the bed 504 (e.g., intersections of the side bed pixels with the back wall 506 pixels, intersections of the side bed pixels with the baseboard pixels, intersection points with the pixels representing the baseboard shifted along the sides of the bed by the length of the bed, etc.). The above description is utilized with the cameras 102 in a first orientation (e.g., baseboard is proximal to the cameras 102 and the head of the bed is distal to the cameras 102). However, it is understood that the cameras 102 may be re-positioned and different techniques may be utilized to define portions of the bed 504 (e.g., baseboard 510 is distal to the camera as compared to the plane of the bed, etc.). For example, the processor 106 may identify the baseboard pixels as having a z-component as distal to the cameras 102 as compared to the z-component of the bed plane pixels.

Once the bed has been identified, the processor 106 identifies one or more object points (pixels) within the field of view (FOV) of the cameras 102. In a specific implementation, the module 128 is configured to identify (e.g., find) points representing the body above the bed (e.g., identify pixels having a depth value closer to the cameras 102 as compared to the depth values of pixels representing the bed). For instance, the module 128 may instruct the processor 106 to determine the gradient change between the depth values of the pixels representing the body 502 to the depth values of the pixels representing the bed 504. In an implementation, the object points may be a grouping of pixels that represent a body region of the subject. For example, the processor 106 may identify pixels that potentially represent feet points (e.g., represent the feet of the subject within the FOV). In another example, the processor 106 may identify pixels that potentially represent leg points, arm points, hand points, and so forth. In an implementation, the processor 106 is instructed to identify pixels that are: proximate to the bed 504 in two-dimensional coordinates (e.g., x and y components of the potential feet pixels are proximal to the bed pixels, which is based upon the bed polygon); the potential foot pixels are sufficiently above the bed pixels (pixels representing the bed plane) in three dimensions; and the potential foot pixels are sufficiently close (e.g., z-component of the pixels are proximal) to the cameras 102. Thus, the point cloud may only include those points identified as representing the feet 514. Additionally, a variety of other filters may be utilized to identify points representing the feet 514. For example, the module 128 is configured to cause the identification of points that are within a certain range of the points representing the hips 516, as well as restricting those identified points that are within a predetermined distance from the center of the bed 504. These points may further be restricted to points that are within a predefined range of angles with respect to the center of the bed. The module 128 may also cause the processor 106 to maintain the points whose rate of change in height in the direction of the identified hip area is large (e.g., greater than a predetermined threshold). For example, the module 128 may cause the processor 106 to maintain points whose rate of change is approximately 0.125 millimeter for every 1 millimeter (e.g., points that move in the direction of the hip). In another implementation, the module 128 may cause the processor 106 to identify pixels distal from the pixels representing the surface of the bed (e.g., pixels having z components that are closer to the cameras 102 as compared to the z components of the pixels representing the surface of the bed 504). For example, the processor 106 may identify pixels having z components ranging from approximately three inches to approximately twelve inches (3 in. to 12 in.) proximal to the cameras 102 as compared to the pixels representing the bed 504 (e.g., pixels are identified that have a z component approximately three inches to approximately twelve inches closer to the cameras 102 as compared to the z-components of the bed 504).

The module 128 is then configured to cause the processor 106 to segment the potential body (e.g., feet) points to isolate one or more body (e.g., feet 514) segments (e.g., a plurality of pixels representing the feet). In an implementation, the processor 106 may utilize an image segmenter to segment the pixels according to predefined parameters. Upon the initial segmentation, the processor 106 may discard smaller segments (e.g., discards segments with fewer than ten (10) points, etc.). Segments that represent the feet may be combined that do not differ horizontally but differ vertically. This may combine extra segments introduced from cloth proximal to the feet. At least substantially all of the feet segment positions (e.g., feet segments identified in earlier frames) may be stored in the memory 108. Thus, if the current potential feet points are identified as a single segment (e.g., feet are touching), the processor 106 can split the current signal segment based upon the positions of the feet segments previously identified (e.g., segments identified in previous frames stored in memory 108). The processor 106 then identifies the pixels representing the feet 514 as the highest remaining segments in the depth mask. It is understood that the module 128 is configured to cause the processor 106 to classify feet segments based upon one or more classified body segments as well. For example, the processor 106 may identify pixels as representing a body. Upon identifying the body pixels, the processor 106 is configured to identify feet pixels based upon the previously identified body pixels.

In another implementation, the module 128 is configure to cause the processor 106 to identify an instruments, such as a pipe-like structure, that the subject may be utilizing in the subject's exercise. In this implementation, the processor 106 scans a sub-set (region) of the depth frame to identify pixels as representing the instrument. The location of the region may be determined by the location of the pixels representing the bed 504. The instrument pixels may be defined as pixels having the same, or at least substantially same, z-component aligned in a linear configuration (e.g., near straight line, etc.) that are within one or more predefined parameters (e.g., linear pixels having a predefined height component above the bed pixels, etc.). Thus, once the processor 106 identifies pixels as potentially representing the instrument, the processor 106 may filter a portion of the identified pixels that have a z-component outside the predefined parameters (e.g., proximal to the baseboard pixels, proximal to the bed pixels, below the bed pixels, etc.). These pixels (points) are then converted to the point cloud to allow for three-dimensional modeling of the instrument. A line is then fitted through the points representing the instrument. In an implementation, the line may be fitted via RANSAC, or another suitable line fitting process. The center of mass of the instrument can be approximated by determining where the line approximately intersects the middle of the environment (e.g., approximately where the line intersects the middle of the screen). A point classifier module (e.g., point tracking module 116) may be utilized to classify the points along the instrument.

The processor 106 is configured to determine three dimensional tracked points (e.g., track the movement of each foot) based upon the feet segments. In an implementation, the module 128 causes the processor 106 to take the mean-shifted center of a subset of points in each identified foot segment that are higher (higher y-component) as compared to the mean shifted center of the remaining subset of points in the foot segment. The module 128 is configured to cause the processor 106 to store the location of each tracked point in the memory 108. The processor 106 is configured to create a weighted distance between the current tracked points and the stored track points that have a greater change in the horizontal directions as compared to the vertical direction. Thus, the processor 106 is configured to measure (e.g., track) the movement of the feet based upon the feet segments.

Figure 5B:
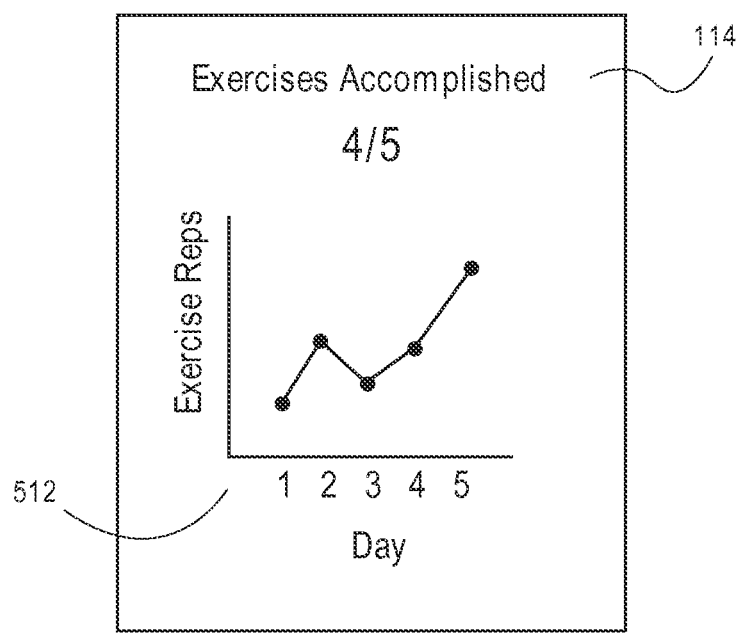
FIG. 5B illustrates a graphical representation of feedback the image capture system is configured to provide based upon the performance of the exercise.

A weighted coefficient may then be determined based upon one or more suitable distribution methods. For example, the processor 106 may utilize a Gaussian distribution of weighted distances to determine a weighted coefficient that decays via a Gaussian distribution over time. Time may be defined as the difference between the time stamps of the current tracked points and the time stamps of the previously tracked points (e.g., tracked points associated with previous frames that are stored in the memory 108). The tracked points may then be passed through one or more parsing algorithms. The processor 106 may then output the weighted sum value of the current tracked points and previously tracked points using this weighted coefficient. The weighted sum value is utilized to reduce jitter associated with the tracked objects. The values may be utilized to monitor the subject's rehabilitation exercise. For example, one or more values may be utilized to generate one or more graphs, values, instructions, reports, or the like, associated with the rehabilitation exercise. Thus, the subject's therapist, doctor, or the like, can monitor the subject's rehabilitation. For example, the processor 106 may be configured to generate an at least near real-time interactive report (see graphical representation 512 shown in FIG. 5B) allowing the subject to view data and/or results associated with the exercise. In another example, the processor 106 may be configured to generate an at least near real-time instruction based upon the exercise. The instruction may include preprogrammed instructions for improving the exercise performed, additional exercises the subject may find of interest, and so forth. The instructions and/or reports may be presented via the display 114, or the like. It is contemplated that the subject may perform varying types of rehabilitation exercises that can be tracked utilizing the system 100.

Example Rehabilitation Tracker Process

Figure 6:
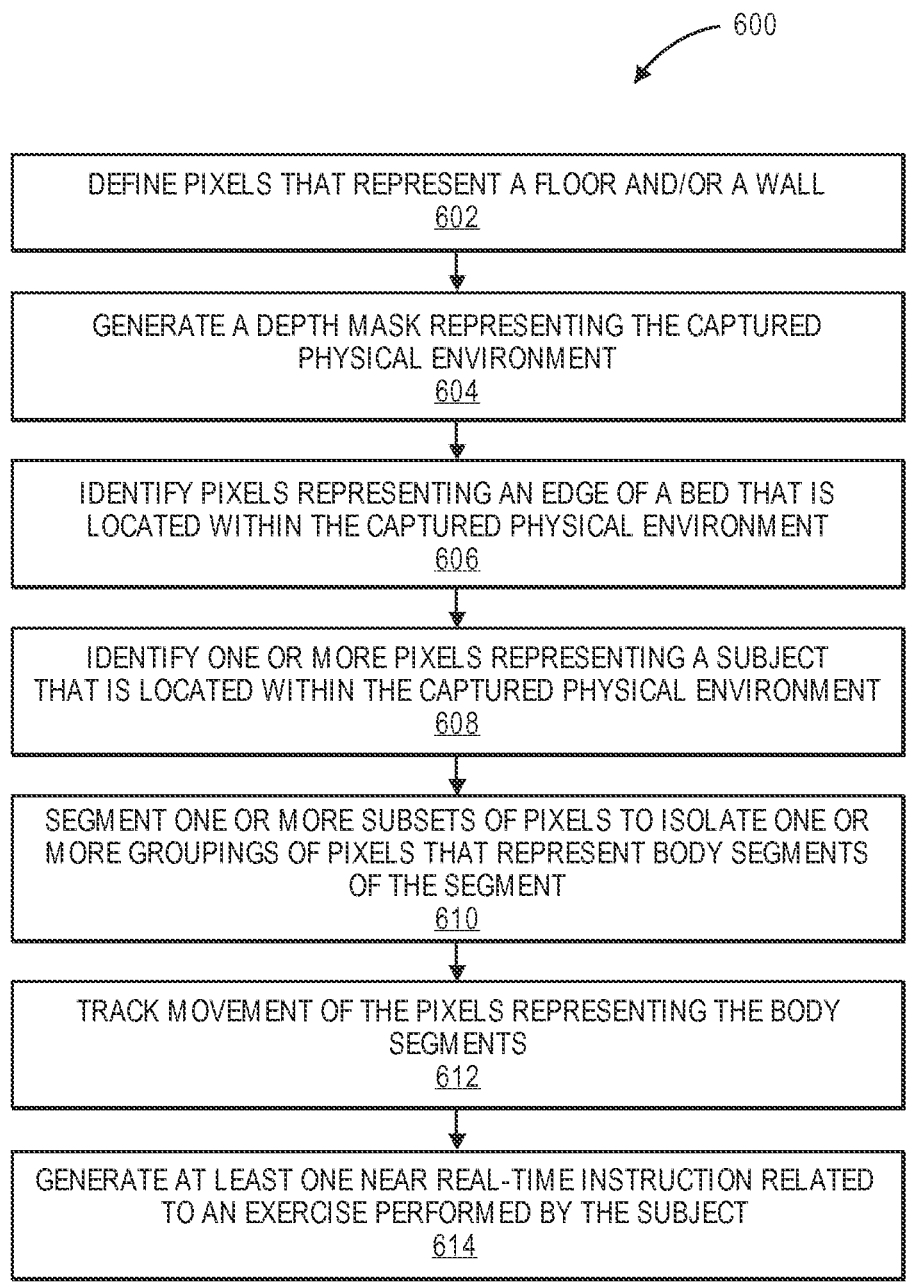
FIG. 6 is a flow diagram illustrating an example process for tracking one or more pixels representing a body segment in accordance with an example implementation of the present disclosure.

FIG. 6 illustrates an example process 600 for tracking a subject's rehabilitation. As described above, the cameras 102 may be positioned proximate (e.g., over, adjacent to) a bed 504 that the subject 502 is utilizing. As shown in FIG. 6, pixels that represent a floor and that represent a wall are defined (Block 602). For example, the module 128 is configured to select pixels having values within pre-defined parameters (e.g., pixels having x, y, z values that are within the pre-defined parameters) as representing a portion of a wall 506 within the FOV of the cameras 102 or a portion of a floor 508 within the FOV of the cameras 102.

A depth mask representing the captured physical environment is generated (Block 604). As described above, the module 128 causes the processor 106 to generate a depth mask (e.g., depth map), which is utilized to identify pixels having a pre-determined gradient change with respect to the adjacent pixels. Pixels representing the edge of a bed are identified (Block 606). For example, as described above, the processor 106 may identify one or more edges 509 of the bed 504 based upon a minimum number of pixels within the line, location (position) of the pixels toward the center of the image, a line of pixels that are spaced approximately the width of the bed 504, and the like. The baseboard 510 of the bed 504 may then be identified. The module 128 is configured to cause the processor 106 to fit a polygon (e.g., an active region that the subject (patient) is located within) to the pixels representing the bed 504.

Once the bed has been identified, one or more pixels representing an object (i.e., the subject) are identified (Block 608). As described above, the module 106 is configured to instruct the processor 106 to identify pixels having a z-value above the bed 504. These pixels may represent an object, such as a patient's feet 514, body, legs, arms, and so forth. As shown in FIG. 6, one or more subsets of pixels are segmented to isolate (e.g., identify) one or more groupings of pixels that represent body segments of the object (Block 610). Based upon the identified body points, the movement of the pixels representing the body points is tracked. (Block 612). An at least near real-time instruction is generated based upon the exercise (Block 614). For example, as described above, the module 128 is configured to instruct the processor 106 to generate an least near real-time instruction, which may include pre-programmed instructions for improving the exercise performed, additional exercises the subject may find of interest, and so forth. The instructions and/or reports may be presented via the display 114, or the like.

Example Body Tracker Implementation

Figure 7A:
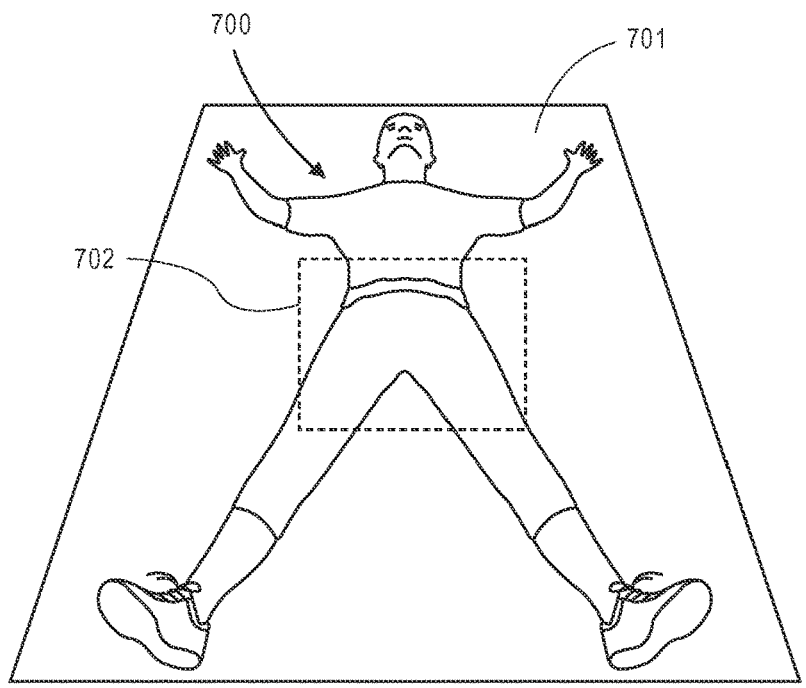
FIGS. 7A through 7F illustrate diagrammatic illustrations for identifying one or more pixels (points) representing a portion of a subject's body and tracking the pixels in accordance with an example implementation of the present disclosure.

As shown in FIG. 1, the computing device 104 further includes a body tracker module 130, which is storable in the memory 108 and executable by the processor 106. The body tracker module 130 is representative of functionality to identify and track one or more portions of a subject's body 700 within the FOV of the cameras 102 (e.g., subject's body 700 is positioned over a bed 701). In an implementation, as shown in FIG. 7A, the module 130 is configured to cause the processor 106 to identify a point (e.g., one or more pixels) of interest 702, or an "anchor point." The point of interest 702 represents one or more pixels that represent the portion of the subject's body 700 that are most likely not going to move while the subject is exercising or moving. In this implementation, the portion of the subject's body refers to the lower portion of the subject's body (e.g., subject's in-seam 704A, subject's crotch area 704B, the subject's legs 704C and 704D, the subject's knees 704E and 704F, the subject's feet 704G and 704H). For convenience, the in-seam refers to the groin portion (i.e., the medial (abductor) compartment of the thigh) of the human body.

The module 130 is configured to cause identification of the anchor point 702 (e.g., groin region) of the subject's body while the subject is in a calibration pose (e.g., patient is staying at least substantially motionless, such as laying in the supine position and not moving for a predefined amount of time). The anchor point 702 may identified as being a group of points (e.g., pixels) that have points directly below, with respect to the orientation of the cameras 102, (in projective space) that are further away from the cameras 102 (i.e., pixels adjacent to or nearly adjacent to the identified point that have greater z-values as compared to the identified point's z-value), as well as points (e.g., pixels) to the lower-left and the lower-right that are closer to the cameras 102.

Figure 7B:
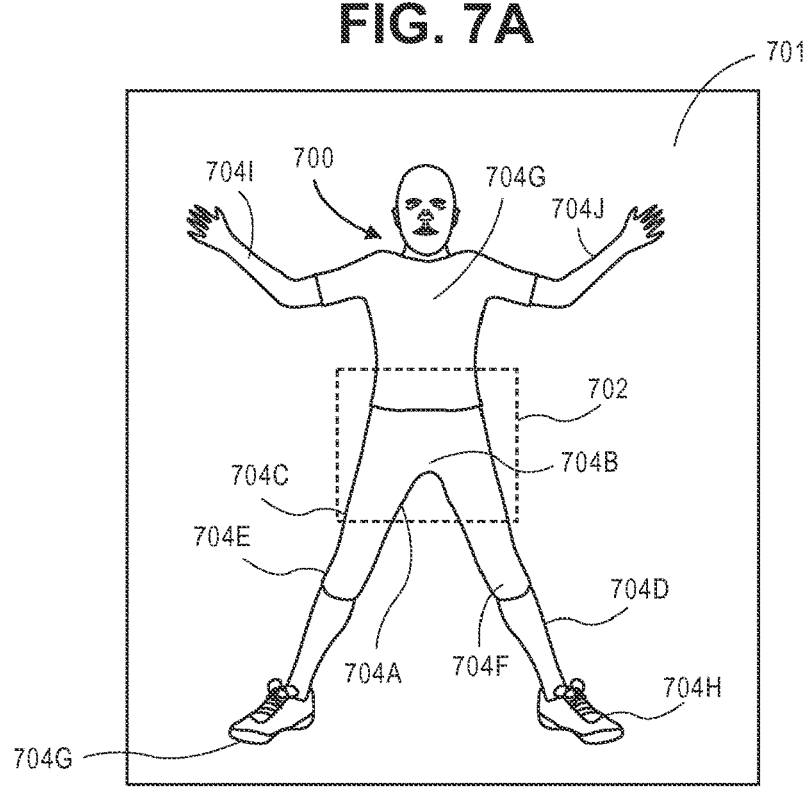

Additionally, the system 100 identifies the kinematics (e.g., system's 100 calibration period) of the subject to allow for identification of various joint positions (i.e., identification of pixels representing joint positions (e.g., knees 704E, 704F) or areas of the subject's body 700) as shown in FIG. 7B. The term "kinematics" or "kinematically" may refer to determining whether a distance value or an angle value between joints is within a plausible range (e.g., determining whether a joint identified as a knee joint has a corresponding angle or distance value is acceptable based upon human knee joint contortions). For example, a knee 704E, 704F can bend ninety (90) degrees backwards; however, the knee cannot bend ninety (90) degrees forwards. Thus, if an identified joint does not fall within an acceptable range, the system 100 is configured to reject the identified joint and utilize the last known best guess value.

It is contemplated that the module 130 may be configured to identify a top portion (e.g., torso, arms, head) of the subject and a bottom portion (e.g., legs, feet, and crotch) of the subject. The module 130 may cause the identification of these portions based upon the identification of pixels that likely represent the corresponding portions of the body (e.g., pixels representing the arms 704I, 704J may have a similar shape or pattern, pixels representing the torso 704K may have a similar shape or pattern, pixels of the body are compared to surround pixels based upon the depth values of the pixels, etc.). Given that the subject may have the subject's legs separated during the calibration period, the module 130 may apply a coefficient that is utilized to scale the subject's length accordingly. In a specific implementation, the module 130 may cause the processor 106 to utilize the legs 704C, 704D as a hypotenuse of a right triangle with respect to the subject's midsection. Thus, the processor 106 may utilize appropriate trigonometric functions to approximate the height of the subject.

Figure 7C:
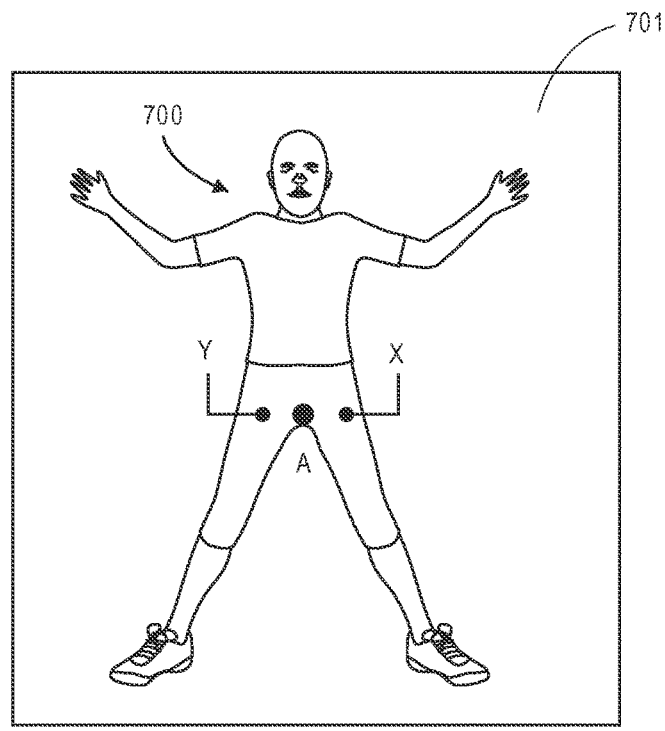

As shown in FIG. 7C, the module 130 is configured to cause the processor 106 to identify the hips (points "X" and "Y") of the subject (e.g., identify pixels representing the hips of the subject). The module 130 may utilize one or more suitable kinematic methods for identifying the various parts of the subject as described herein. For example, as shown in FIG. 7C, the module 130 may cause the processor 106 to identify a particular distance above the in-seam and which are at least approximately equidistant from a line separating the subject in half (where the line intersects the defined in-seam point (e.g., pixel(s)). For convenience, point A represents the mid-section of the subject's body 700. It is contemplated that these identified pixels remain at least substantially constant due to the subject lying in a steady supine position in the bed 701.

Figure 7D:
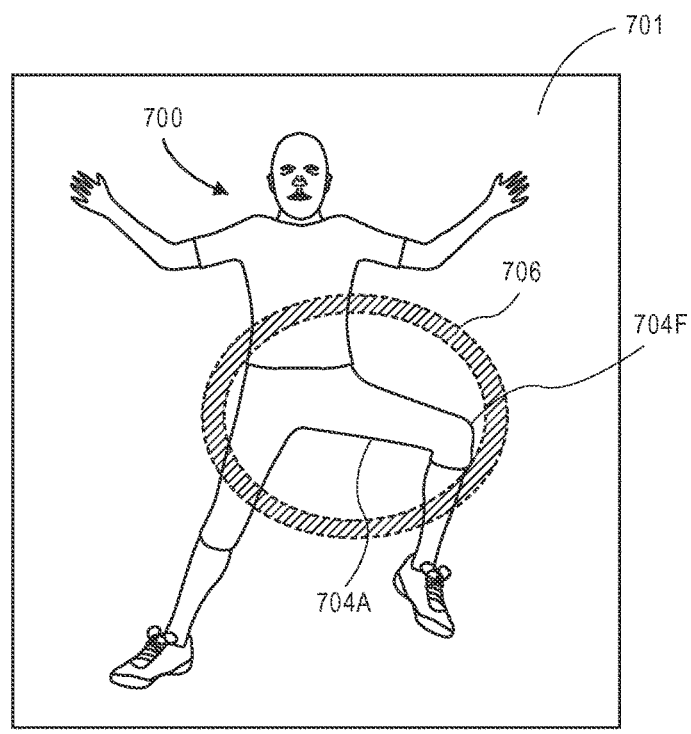

The module 130 is then configured to cause identification pixels representing the knees of the subject. In an implementation, the module 130 causes the processor 106 to determine (e.g., inspect) one or more pixels (or points) that are within a predefined distance (e.g., a range of distances) from the in-seam and that have a depth value within a pre-defined range are knee points (e.g., pixels representing knees of the subject). For descriptive purposes, as shown in FIG. 7D, a region 706 centered around the in-seam point 704A is created to illustrate a pre-defined range of distances. A circle region 706 is illustrated for illustrative purposes. These distances are utilized to identify pixels to inspect to determine whether the pixels represent a portion of the subject's knee 704F. Continuing with this descriptive illustration, the pixels that intersect the region 706 are examined (inspected) for the purposes of determining whether pixels represent the subject's knees. Thus, in a specific implementation, the pixels having x-values and y-values corresponding to the pre-defined distance are examined to determine whether those pixels represent the subject's knees.

Figure 7E:
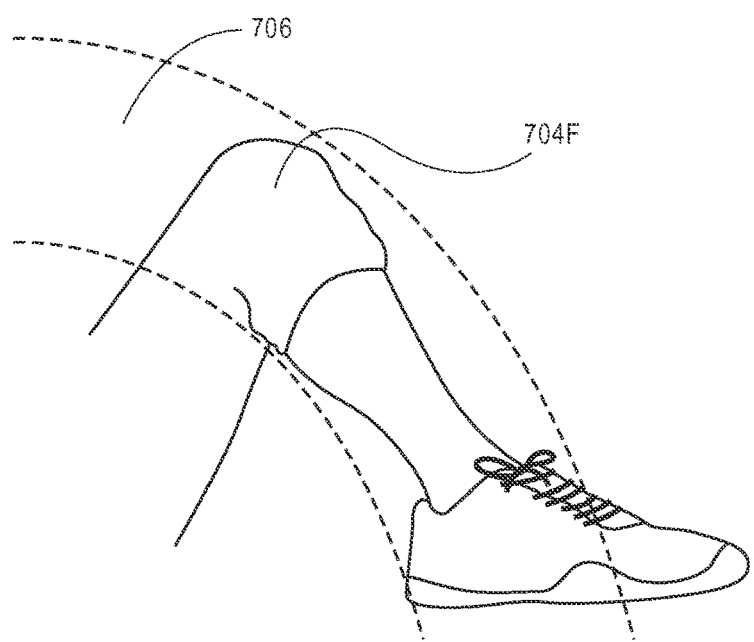
Figure 7F:
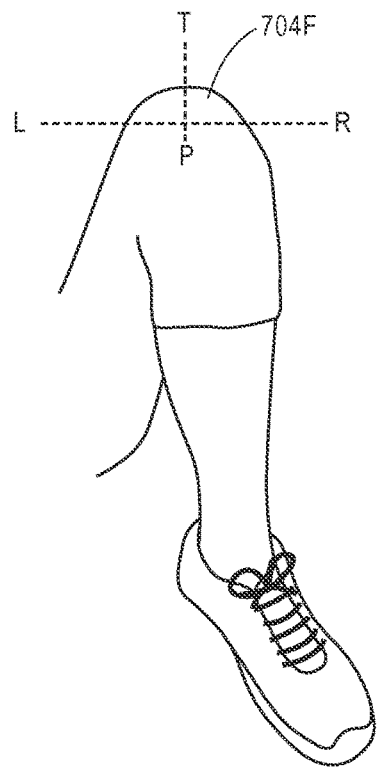

However, it is contemplated that a problem may arise if the subject re-positions the knees or the knees are not within the pre-defined distance (see FIG. 7E). Thus, the module 130 may utilize a point-classifier identification process (similar to the point-classifier module 116 described above) to compensate or to replace the kinematic-identified points, as described in greater detail above. In an implementation, as shown in FIG. 7F, one or more points (pixels) are examined and identified as being a particular distance further from (e.g., larger depth value as compared to) a point of interest (pixel of interest). For example, points T, L, and R represent pixels having depth values that are greater, which represent a further distance from the cameras 102, as compared to the point P. Thus, P may be identified as a possible knee point. This process may be used to either further filter other leg points or to identify knee points when no valid knees are identified kinematically. In one or more implementations, a machine-learned classifier (as described herein) may also be applied to the process of identifying (e.g., finding, determining) knees or other body points. Moreover, in the event the knee is partially obscured by other body parts (e.g., legs, arms) or other objects within the FOV (e.g., clinician, bed sheets, etc.), the last known identified position is maintained in the memory 108. Adjustments (in order to maintain kinematic restraints) may be utilized while the point is obscured in order to create a best-guess estimate of the position of the body joint.

It is contemplated that the once the points (pixels) representing the various portions of the subject's body, the module 130 causes the processor 106 to monitor one or more exercises that the subject performs. For instance, the module 130 may cause the processor 106 to continually identify and monitor the positions of the identified pixels frame to frame (e.g., image frame to image frame). Based upon the continuous monitoring, the module 130 causes the processor 106 to measure the exercises performed. For instance, the subject may be instructed to move the subject's foot/ankle region as part of the subject's rehabilitation regimen. Thus, the system 100 is configured to measure the movement of the foot/ankle region and provide information to the subject's doctor/physical therapist relating to the movement of the ankle (e.g., how far the subject moved the foot/ankle region, how many times the exercise was performed, a graphical representation of the movement of the foot/ankle region, etc.). Moreover, it contemplated that the present disclosure may be utilized to identify the upper-body portions of the subject while the subject is in a calibration position (e.g., supine position, seated position, standing position, etc.). The module 130 may be configured to instruct the processor 106 to cause the display of data relating to the exercises to medical personnel (e.g., subject's physical therapist, subject's doctor, subject's nursing assistant, etc.). For example, the processor 106 may be instructed to cause the display of graphical representations (similar to the graphical representations 512 illustrated in FIG. 5B) relating to the exercises performed by the subject.

Example Rehabilitation Tracker Process

Figure 8:
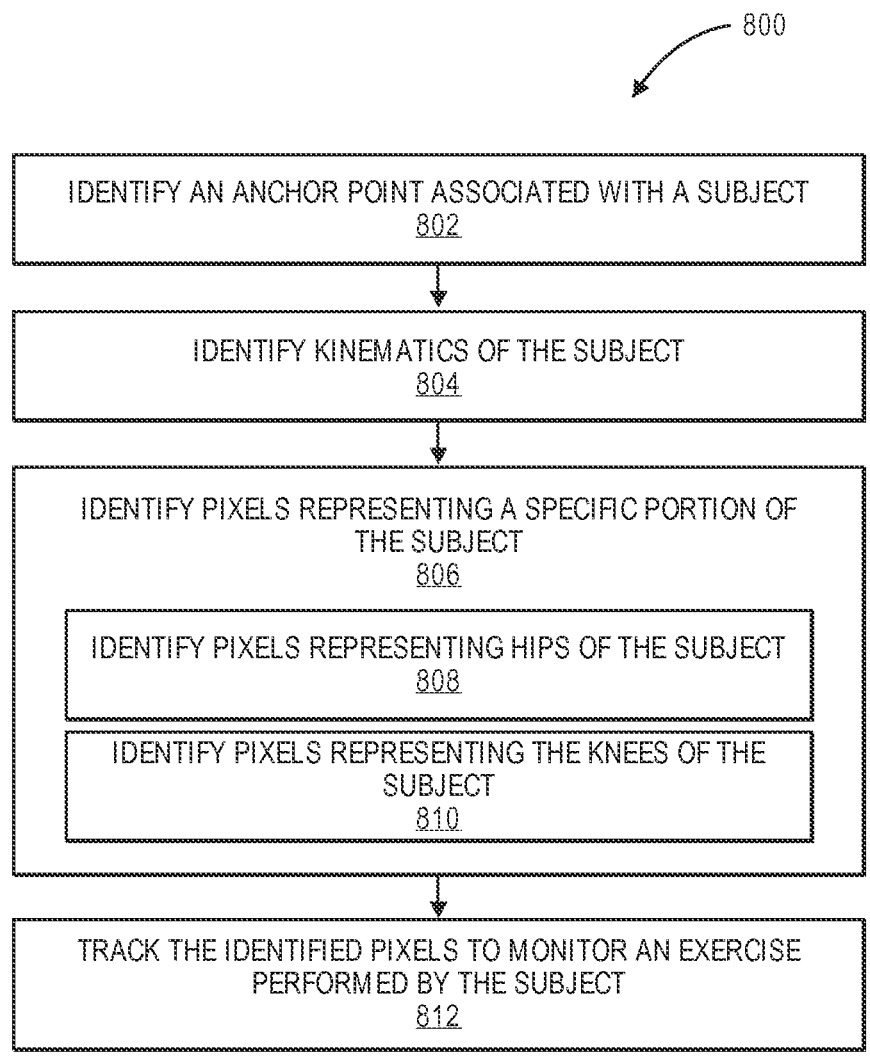
FIG. 8 is is a flow diagram illustrating an example process for tracking one or more one or more portions of a body of a subject in accordance with an example implementation of the present disclosure.

FIG. 8 illustrates an example process 800 for tracking one or more portions of a body of a subject (e.g., patient). As shown in FIG. 8, an anchor point associated with a subject is identified (Block 802). As described above, the anchor point comprises one or more points (e.g., one or more pixels) of interest. The point of interest represents one or more pixels that represent the portion of the subject's body that is most likely not going to move while the subject is exercising or moving. Once an anchor point is identified, the kinematics of the subject are identified (Block 804). In other words, the system 100 is calibrated based upon an at least substantially non-moving subject within the FOV of the cameras 102. As shown in FIG. 8, pixels representing a specific portion (e.g., a hip, etc.) of the subject are identified (Block 806). As described above, one or more suitable kinematic methods may be utilized to identify pixels representing various parts of the subject, such as the hip portions of the subject. For instance, pixels representing the hips of the subject may be first identified (Block 808). Upon identifying the pixels representing the hips, pixels representing the knees of the subject are identified (Block 810).

Upon identifying the pixels representing the various portions, or parts, of the subject's body, the pixels are tracked to monitor an exercise performed by the subject (Block 812). In one or more implementations, the module 130 may cause the processor 106 to continually identify and monitor the positions of the identified pixels frame to frame (e.g., image frame to image frame). Based upon the continuous monitoring, the module 130 causes the processor 106 to measure the exercises performed. By continuously monitoring the exercises performed, the module 130 may be configured to instruct the processor 106 to furnish data relating to the exercises to medical personnel, such as the subject's physical therapist, the subject's doctor, and so forth.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims. A person skilled in the art will recognize that portions of the present disclosure may be implemented in hardware, software, firmware, combinations thereof, and so forth.

What is claimed is:

1. A computer-implemented method comprising:
   receiving, via a processor in near-real time, a depth mask representing a captured physical environment via a depth sensing device;
   identifying, via the processor in near-real time, a three-dimensional model representing a bed within the captured physical environment, wherein the processor is configured to scan the depth mask to identify pixels having a predetermined gradient change and identifies the bed based upon the predetermined gradient change of the pixels;
   identifying, via the processor in near-real time, a three-dimensional model representing a subject located within the captured physical environment based on a gradient change between pixels representing an object over the bed and the pixels representing the bed;
   defining a three-dimensional active region based upon the three-dimensional model representing the bed;
   segmenting the three-dimensional model representing the subject to isolate a body of the subject;
   identifying an anchor point corresponding to the body, wherein the anchor point represents a non-moving portion of the body within the three-dimensional model;
   identifying a joint of the body within the three-dimensional model;
   determining whether the joint is within a predefined distance of the anchor point; and
   tracking, via the processor in near-real time, the body through a plurality of image frames to track movement performed by the subject within the three-dimensional active region when the joint is within the predefined distance of the anchor point.

2. The computer-implemented method as recited in claim 1, further comprising:
   generating an at least near real-time interactive report based on tracked movement performed by the subject within the three-dimensional active region.

3. The computer-implemented method as recited in claim 1, further comprising identifying a three-dimensional model representing a floor within the captured physical environment.

4. The computer-implemented method as recited in claim 3, further comprising identifying the three-dimensional model representing the bed within the captured physical environment by comparing a depth value of at least one pixel of the three-dimensional model representing the bed with at least one of a depth value of at least one pixel of the three-dimensional model representing the floor or a depth value of at least one pixel of the three-dimensional model representing the subject.

5. The computer-implemented method as recited in claim 3, further comprising identifying the three-dimensional model representing the subject associated with the depth mask as representing the subject within the captured physical environment by comparing a depth value of at least one pixel of the three-dimensional model representing the subject with a depth value of at least one pixel of the three-dimensional model representing the floor or a depth value of at least one pixel of the three-dimensional model representing the bed.

6. The computer-implemented method as recited in claim 1, wherein the anchor point corresponds to an in-seam of the subject.

7. The computer-implemented method as recited in claim 1, wherein the joint corresponds to a knee of the subject.

8. The computer-implemented method as recited in claim 1, wherein the movement comprises an exercise performed by the subject.

9. A computer-implemented method comprising:
receiving, via a processor in near-real time, a depth mask representing a captured physical environment via a depth sensing device;
identifying, via the processor in near-real time, a three dimensional model representing a bed within the captured physical environment, wherein the processor is configured to scan the depth mask to identify pixels having a predetermined gradient change and identifies the bed based upon the predetermined gradient change of the pixels;
identifying, via the processor in near-real time, a three-dimensional model representing a first portion of the bed based on a gradient change between pixels representing an object over the bed and the pixels representing the first portion of the bed;
identifying, via the processor in near-real time, a three-dimensional model representing a second portion of the bed based on a gradient change between pixels representing an object over the bed and the pixels representing the second portion of the bed;
defining a three-dimensional active region based upon the three-dimensional model representing the first portion of the bed and the three-dimensional model representing the second portion of the bed;
identifying a body within the three-dimensional active region;
identifying an anchor point corresponding to the body, wherein the anchor point represents a non-moving portion of the body within the three-dimensional model;
identifying a joint of the body within the three-dimensional model; and
determining whether the joint is within a predefined distance of the anchor point.

10. The computer-implemented method as recited in claim 9, further comprising identifying a three-dimensional model representing a floor within the captured physical environment.

11. The computer-implemented method as recited in claim 9, further comprising identifying a three-dimensional model representing a wall within the captured physical environment.

12. The computer-implemented method as recited in claim 9, further comprising identifying the three-dimensional model representing a first portion of the bed based upon comparing a depth value at least one pixel of the three-dimensional model representing the first portion of the bed as compared to a depth value of at least one pixel of the three-dimensional model representing the second portion of the bed.

13. The computer-implemented method as recited in claim 9, wherein the anchor point corresponds to an in-seam of the body and the joint corresponds to a knee of the body.

14. A computer-implemented method comprising:
receiving, via a processor in near-real time, a depth mask representing a captured physical environment via a depth sensing device;
identifying, via a processor in near-real time, a three-dimensional model representing a bed within the captured physical environment, wherein the processor is configured to scan the depth mask to identify pixels having a predetermined gradient change and identifies the bed based upon the predetermined gradient change of the pixels;
identifying, via a processor in near-real time, a first position of the bed within the captured physical environment based upon the three-dimensional model representing the bed based upon the predetermined gradient change of the pixels;
identifying, via a processor in near-real time, a second position of the bed within the captured physical environment based upon the three-dimensional model representing the bed based upon the predetermined gradient change of the pixels;
defining a three-dimensional active region based upon the three-dimensional model representing the bed;
identifying a body within the three-dimensional active region;
identifying an anchor point corresponding to the body, wherein the anchor point represents a non-moving portion of the body within the three-dimensional model;
identifying a joint of the body within the three-dimensional model; and
determining whether the joint is within a predefined distance of the anchor point.

15. The computer-implemented method as recited in claim 14, further comprising generating a weighted sum value based on current tracked points corresponding to a body segment and previously tracked points corresponding to the body segment; and tracking the body segment based on the weighted sum value through a plurality of image frames to track movement performed by a subject within the three-dimensional active region.

16. The computer-implemented method as recited in claim 14, further comprising identifying, in a first image frame of a plurality of image frames captured by depth sensing device, the first position of the bed within the captured physical environment based upon the three-dimensional model representing the bed; and identifying, in a second image frame of the plurality of image frames, the second position of the bed within the captured physical environment based upon the first position of the bed.

17. The computer-implemented method as recited in claim 16, wherein the plurality of image frames comprise a plurality of successive image frames.

18. The computer-implemented method as recited in claim 14, further comprising identifying at least one of a three-dimensional model representing a floor or a three-dimensional model representing a wall.

19. The computer-implemented method as recited in claim 14, further comprising identifying, in a first image frame of a plurality of image frames captured by depth sensing device, the first position of the bed within the captured physical environment by comparing a depth value of at least one first pixel of the three-dimensional model representing the bed associated with the first image frame with a depth value of at least one second pixel of the three-dimensional model representing the bed associated with the first image frame; and identifying, in a second image frame of the plurality of image frames, the second position of the bed within the captured physical environment by comparing a depth value of at least one first pixel of the three-dimensional model representing the bed associated with the second image frame with a depth value of at least one second pixel of the three-dimensional model representing the bed associated with the second image frame.

* * * * *